US005969094A

United States Patent [19]
Compans et al.

[11] Patent Number: 5,969,094
[45] Date of Patent: Oct. 19, 1999

[54] ANTI-PARAMYXOVIRUS SCREENING METHOD AND VACCINE

[75] Inventors: Richard William Compans, Atlanta; Qizhi Yao, Decatur, both of Ga.

[73] Assignee: Emory University, Atlanta, Ga.

[21] Appl. No.: 08/651,420

[22] Filed: May 22, 1996

Related U.S. Application Data

[63] Continuation-in-part of application No. 08/135,285, Oct. 12, 1993, Pat. No. 5,550,017.

[51] Int. Cl.$^6$ .................................................. A61K 38/16
[52] U.S. Cl. .............................. 530/324; 530/325; 435/5
[58] Field of Search ...................... 435/5, 69.7; 530/324, 530/325; 424/186.1

[56] References Cited

U.S. PATENT DOCUMENTS 5,550,017  8/1996  Compans ..................................... 435/5

OTHER PUBLICATIONS

Varsanyi et al., "Molecular cloning and sequence analysis of human parainfluenza type 2 virus mRNA encoding the fusion glycoprotein", Journal of General Virology, vol. 72, pp. 89–95, 1991.

Cote et al., "Nucleotide sequence of the coding and flanking regions of the human parainfluenza virus type 3 fusion glycoprotein gene", Jouranal of General Virology, vol. 68, pp. 1003–1010, 1987.

Blumberg et al., "Sequence determination of the Sendai virus HN gene and its comparison to the influenza virus glycoproteins", Cell, vol. 41, pp. 269–278, May 1995.

Lounsbach, G.R. et al. "Binding of neutralizing monoclonal antibodies to regions of the fusion protein of respiratory syncytial virus expressed in *Escherichia coli*"; *Journal of General Virology* (1993) 74:2559–2565.

Precious, B. et al. "Sequence Analysis of the HN gene parainfluenza virus type 2"; *Journal of General Virology* (1990) 71:1163–1168.

Heminway et al. (1994) *Virus Research* –31:1–16.
Sergel et al. (1993) *Virology* 196:831–834.
Sergel et al. (1993) *Virology* 193:717–726.
Tsurudome et al. (1995) *Virology* 213:190–213.
Deng et al. (1996) *Virology* 209:457–469.
Bousse et al. (1994) *Virology* 204:506–514.
Yuasa et al. (1995) *Virology* 206:1117–1125.
Yao et al. (Nov. 1995) *J. of Virology* 69:7045–7053.
Sergel–Germano et al. (Nov. 1995) *J. of Virology* 68:7654–7658.
Reitter et al. (Oct. 1995) *J. of Virology* 69:5995–6004.
Tanabayashi et al. (May 1993)*J. of Virology* 67:2928–2931.
Rapaport et al. (1995) *The EMBO Journal* 14:5524–5531.

*Primary Examiner*—Marian C. Knode
*Assistant Examiner*—Brenda G. Brumback
*Attorney, Agent, or Firm*—Greenlee Winner and Sullivan P.C.

[57] ABSTRACT

A method is provided for detecting whether a test composition can inhibit cell fusion mediated by paramyxovirus infection. A method is also provided for identifying an antiviral peptide capable of inhibiting paramyxovirus-induced cell fusion. The methods are based on the discovery that the hemagglutination and fusion-inducing proteins of paramyxoviruses interact to form a complex termed HN:F, that is prerequisite to cell fusion. Antibodies to HN:F provide a novel means of providing improved immunity against paramyxovirus infection.

4 Claims, 11 Drawing Sheets

Parainfluenza 2 virus HN gene restriction map

```
      DraI  NsiI  Eco57I BglII FauI FokI        EcoRI      HhaI
0     308   320   627    748  886  983          1289       1540        1713
```

FIG. 5A

Simian virus 5 HN gene restriction map

```
      PstI BsiI        GsuI       HgiAI      AflIII  HgiEII  BsaBI NruI ThaI
      239  332         751        904        1180    1771    1500  1506 1506
0                                                                              1695
```

FIG. 5B

| 2F1B21 (21 A.A.) | KSAEDWIADSNFFANQARTAK |
| 2F1B34 (34 A.A.) | DLSNQINSINKSLKSAEDWIADSNFFANQARTAK |

| 3F1B24 (24 A.A.) | ELNKAKSDLEESKEWIRRSNQKLD |
| 3F1B34 (35 A.A.) | ELNKAKSDLEESKEWIRRSNQKLDSIGNWHQSST |

ANTI-PARAMYXOVIRUS SCREENING METHOD AND VACCINE

This application is a continuation-in-part of Ser. No. 08/135,285 filed Oct. 12, 1993 now U.S. Pat. No. 5,550,017.

FIELD OF THE INVENTION

The invention relates to viruses, specifically paramyxoviruses, including structural aspects of virus components and methods of therapy and prevention of virus infection.

BACKGROUND OF THE INVENTION

The paramyxoviruses infect both humans and animals. The group includes well-known human pathogens such as parainfluenza viruses of which several types are known, measles virus, mumps virus, and respiratory syncytial virus. Among the animal-pathogenic paramyxoviruses are canine distemper virus, rinderpest virus, and Newcastle disease virus. The paramyxoviruses are single-stranded RNA viruses. The virus particles have an outer membrane with short projecting spikes, and an inner nucleocapsid. The spikes include two glycoproteins of relevance, a hemagglutinin with neuraminidase activity (HN) and a cell fusion-inducing protein (F).

Pathogenesis and virus spread through the infected host are both facilitated by virus-mediated cell fusion. Recent work has demonstrated that both HN and F are required for cell fusion to occur [Hu, X. et al. (1992) *J. Virol.* 66:1528–1534; Morrison et al. (1991), *J. Virol.* 65:813–822; Katzir, Z. et al. (1989) *Biochemistry* 28:6400–6405; Ebata, S. N. et al. (1991) *Virology* 183:437–441]. The genes encoding HN and F, respectively, have been cloned from several virus types, including Sendai (SN), simian virus 5 (SV5) parainfluenza type 1 (PI1), parainfluenza type 2 (PI2), and parainfluenza type 3 (PI3). The respective proteins have been purified and various polyclonal and monoclonal antibodies against them have been obtained. Substantial sequence differences exist between the respective HN and F proteins of SN, PI1, PI2, and PI3, although the greatest sequence similarities exist between SN and PI1 [Matsuoka, Y. et al. (1990) *Virus Res.* 16:107–114; Blumberg, B. et al. (1985) *Cell* 41:269–278; Elango, N. et al. (1986) *J. Virol.* 57:481–489; Merson, J. R. et al. (1988) *Virology* 167:97–105; Millar, N. et al. (1986) *J. Gen. Virol.* 67:1917–1927]. HN and F can be expressed either individually or together in HeLa-T4 cells using a vaccinia-T7 recombinant virus vector system [Fuerst, et al. (1986) *Proc. Nat'l. Acad. Sci. USA* 83:8122–8126].

Various experimental approaches have been taken in an attempt to further define the respective roles of HN and F in cell fusion. The possibility of direct association of HN and F has been considered, however, the evidence to date has been negative. Initial studies by Markwell, M. A. K. and Fox, C. F. (1980) *J. Virol.* 33:152–166 demonstrated that HN of Sendai and Newcastle disease viruses exists as a disulfide linked homodimer. The authors also studied spatial relationships of viral proteins by observing the effects of chemical cross-linking reagents on proteins of the mature virus. Interactions up to 1.1 nm distance were expected to be detectable. The NP (nucleoprotein) and M (membrane) proteins were cross-linked by the reagents. Also the F protein could be cross-linked to itself, suggesting that F exists in the native virus as noncovalent homo-oligomers. No close association between HN and F was observed in the cross-linking studies. Sechoy, O. et al. (1987) *J. Biol. Chem.* 262:11519–11523 extended the previous study with respect to F, using a system of purified F in reconstituted lipid vesicles. The authors concluded that native F exists as a noncovalent association of homo-tetramers, each consisting of two peptides, $F_1$ and $F_2$, linked by a disulfide bond. ($F_1$ and $F_2$ are formed by posttranslational cleavage of a precursor, $F_0$ [Scheid, A. and Choppin, P. W. (1974) *Virology* 57:475–490; Homma, M. and Ohuchi, M. (1973) *J. Virol.* 12:1457–1465]. Citovsky, V. et al. (1986) *J. Biol. Chem.* 261:2235–2239 studied HN and F in reconstituted lipid vesicles by circular dichroism. HN and F were purified from detergent-extracted virus particles. The circular dichroism spectrum of vesicles reconstituted with both HN and F was shifted with respect to the spectra of vesicles reconstituted with HN or F alone. The authors inferred a changed conformation of the glycoproteins of the HN-F vesicles, possibly as the result of action of HN upon F. Nakanishi, M. et al. (1982) *Exp. Cell Res.* 142:95–101 also studied purified HN and F in reconstituted vesicles, using diphtheria toxin A fragment to confer cytotoxicity on the vesicles and varying proportions of HN and F. Optimum cytotoxicity of the vesicles was observed when the ratio of F to HN was two. Roux, L. (1990) *Virology* 175:161–166 studied the interaction of HN and F with the immunoglobulin heavy chain binding protein (BiP) by measuring the amount of HN or F precipitated by a monoclonal antibody to BiP. BiP belongs to the heat shock family. It is proposed to function as a "chaperon" protein to aid in maintaining proper folding of other nascent proteins during maturation. Anti-BiP antibody was found to precipitate HN in infected cells, along with BiP, however, only one-fifth as much F was coprecipitated as HN. Katzir, Z. et al. (1989) *Biochemistry* 28:6400–6405 set out specifically to test whether F-HN complexes are formed in infected cell membranes. The authors measured fluorescence photobleaching recovery as a measure of each component's lateral mobility in the membrane. One component was immobilized with an antigen and the effect on mobility of the other, labeled with a fluorophore, was investigated. The authors did not find any effect of HN on lateral mobility of F, or vice-versa, suggesting that no HN-F complexes formed. For a general review, see Morrison T. and Portner, A. (1991) *Structure*, function and processing of the glycoproteins of Paramvxoviridae, In *The Paramyxoviruses* (D. W. Kingsbury ed.) Plenum Publishing Co., New York, pp. 347–382.

SUMMARY OF THE INVENTION

The present invention includes a method for detecting whether a test composition can inhibit cell fusion mediated by paramyxovirus infection. The method is based on the discovery that the HN and F glycoproteins of paramyxoviruses interact with one another to form a complex, termed an "HN:F complex" or simply "HN:F" herein, that can be isolated, and that HN:F complex formation is a prerequisite for cell fusion. Accordingly, by measuring the amount of HN:F complex formed in the membranes of transformed host cells expressing type-homologous HN and F proteins in the presence and absence of various test compositions, the effectiveness of such compositions to inhibit virus-mediated cell fusion can be measured. The term "type-homologous" is used herein to denote that the HN and F components are of the same virus type. As disclosed herein, HN:F complexes are not formed if the HN and F components are of different virus type, except for PI1 and SN, which are defined as "type-homologous." Any pair of virus strains are type-homologous if they can form hetero-HN:F complexes with one another and are not type-homologous if they cannot.

The regions of HN and F Proteins which interact with one another have been mapped by complementary strategies. A region of HN responsible for type-homologous interaction with F has been mapped by means of a series of chimeric HN structures. A peptide fragment of an F protein has been found to function as an inhibitor of type-homologous cell fusion. Other peptides, based, e.g. upon the HN sequence conferring type homology, can be synthesized to inhibit cell fusion. Methods of treating paramyxovirus infection are therefore made feasible, using a peptide that inhibits virus-induced cell fusion as a therapeutic agent. Further development will lead to modified peptides and analog compounds that retain the function of inhibiting paramyxovirus-induced cell fusion.

Another aspect of the invention is a consequence of the fact that antibody specificity of an HN:F complex differs from that of either HN or F alone. Novel antibodies to an HN:F complex exert a unique protective effect by interfering with cell fusion and cell-cell virus transfer. The invention therefore provides a novel antigen and vaccine produced therefrom to provide more complete immunity against paramyxoviruses than was available heretofore.

BRIEF DESCRIPTION OF THE FIGURES

FIG. 5 shows restriction maps of the PI2-HN gene (upper line) and SV5-HN gene (lower line). Vertical lines show relative positions of restriction sites, as labeled. Numbers refer to the nucleotide position of the 5'-nucleotide at each cleavage site, numbered from the first A of the initiation codon.

DETAILED DESCRIPTION OF THE INVENTION

Figure 1:
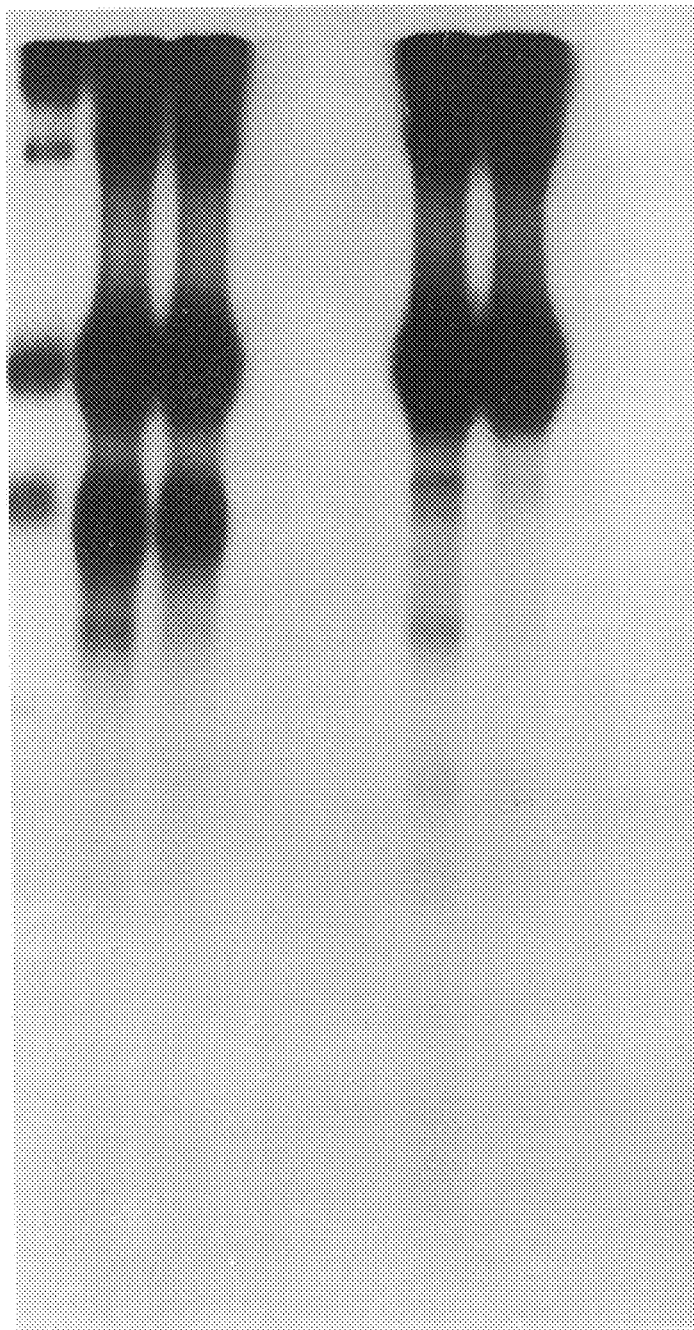
FIG. 1 shows SDS-PAGE separations of labeled proteins in the cross-linking/coprecipitation experiment described in Example 1. The positions of HN and F glycoproteins are indicated on the left. Lane numbers are indicated at the top.

The paramyxoviruses are unique in having both a fusion protein (F) and a hemagglutinin-neuraminidase protein (HN). (In one subgroup, the morbilliviruses, neuraminidase activity is lacking in the hemagglutinin protein). The cell fusions caused by these viruses are the result of activities of the HN and F proteins, or their counterparts. The experiments described herein have been performed with strains of parainfluenza viruses and the closely homologous Sendai virus. The findings described herein, and their applications, will be understood to apply to any paramyxovirus and thus to have application to the entire range of paramyxovirus diseases of animals and humans.

The abbreviation "HN" is used herein to signify the paramyxovirus hemagglutinin-neuraminidase glycoprotein or its morbillivirus counterpart. The HN glycoprotein genes of several paramyxoviruses have been cloned and sequenced.

The abbreviation "F" is used herein to signify the fusion protein of paramyxoviruses. Several F glycoprotein genes of different paramyxovirus strains have been cloned and sequenced.

The abbreviation "HN:F" denotes the complex, newly discovered as a facet of the present invention, which is formed in naturally infected cells or in cells transformed with DNA encoding HN and F. As detailed herein, the HN:F complex can be immunoprecipitated by antibody to either of its components, HN or F. The HN:F complex is disrupted by conditions of SDS-PAGE, suggesting that the complex is not stabilized by a covalent bond between the HN and F moieties. Further, an HN:F complex is only formed between type-homologous components, as herein defined. For example, HN of parainfluenza type 2 (PI2-HN) can form an HN:F complex with F glycoprotein of the same type (PI2-F) but not with F of a different type, e.g., PI3-F. The same holds for reciprocal combinations and for all combinations tested, in both naturally infected cells and transformed cells. The formation of an HN:F complex correlates completely with cell fusion. Cell fusion only occurs under conditions where HN:F complex formation occurs. Conversely, no cell fusion occurs under conditions where HN:F complex formation does not occur, for example, where host cells are cotransformed with PI2-HN and PI3-F. Therefore, HN:F is required for cell fusion.

Type-specificity of the paramyxoviruses has been classified by immunological characteristics, which are conferred by the district antigens of the virus: HN, F and an internal nucleocapsid protein termed NP. Other distinctions, such as host-range or nature of pathogenic symptoms have resulted in certain related viruses having received different names. For example, when amino acid sequences of their HN and F proteins are compared, SV5 and PI2 are seen to be more closely related to one another than to other parainfluenza types. Therefore, for the purposes herein, "type-specificity" is used to include any criterion applied to paramyxoviruses by which the viruses are distinguished from one another.

"Type-homologous" is the term used herein to express the relationship of virus strains which are so closely homologous as to permit mixed HN:F complexes to form upon mixed infection or cotransformation. Only one example is presently known. Sendai virus and PI1 are type-homologous. These two strains also have the most closely homologous HN and F glycoprotein amino acid sequences of any of the paramyxoviruses for which data is available. Other such closely related, type-homologous strains may, of course, exist. They will be readily recognizable by their ability to form HN:F complexes upon mixed infection or cotransformation.

In certain of the procedures described herein, proteins are identified by means of a label which provide sufficient sensitivity to detect and/or measure the small amounts of proteins produced. Any material that can provide the requisite sensitivity, incorporated into the glycoprotein either during translation or posttranslationally can be employed as a matter of choice by those skilled in the art who practice the invention. The examples herein employ methionine labeled with a sulfur isotope, $^{35}S$, as a convenient precursor label. Nevertheless, the terms "label" and "labeling" are to be construed as including such other labels as may be known to those skilled in the art. A "labeled protein precursor" means a labeled amino acid or amino acid precursor which becomes incorporated into protein in the course of cell metabolism.

An HN:F complex includes two components, a first component which may be designated either as HN or F, and a second component, which is the remaining component, either HN or F depending on which of the two is designated as the first component. It is convenient to isolate HN:F by a specific binding agent, such as an antibody, able to combine preferentially with one of the two components, or to the HN:F complex. If the complex is isolated by means of an antibody to a first component, the amount of complex can be quantitatively measured by means of a reagent, such as a labeled antibody, which specifically binds the second component. The subfraction that is isolated by antibody to the first component contains both HN:F and any free, noncomplexed first component which may exist, but any free, unbound second component remains behind. If HN:F is isolated by means of a reagent, such as an antibody specific for the HN:F, the free, noncomplexed first and second components are left behind. The amount of HN:F complex can then be measured by a labeled reagent, such as an antibody, specific for either of the components.

Without directly measuring HN:F complex, it is possible to measure cell fusion quantitatively as an indirect measure of complex formation. Two cell types are used, one having a reporter gene under control of a heterologous promoter that requires a heterologous RNA polymerase, the other expressing the required heterologous polymerase. Fusion of the two cell types allows the RNA polymerase of one cell type to transcribe the reporter gene of the other cell type. As described below in detail, one cell type expressed T7 RNA polymerase. The other cell type bore a β-galactosidase gene controlled by a T7 promoter. Fusion of the two types allowed expression of the β-gal gene, which was measured spectrophotometrically using a chromogenic substrate. The assay can be used to measure either fusion caused by expression of HN and F by transfected cells or induced by viral infection.

Being able to measure the amount of HN:F complex formed under various conditions, for example, in the presence and absence of a putative inhibitor of HN:F complex formation, provides a means for screening potential antiviral agents. Any compound or composition having the ability to either prevent HN:F complex formation or disrupt preexisting HN:F complexes can inhibit virus-induced cell fusion and thereby function as an antiviral agent. By comparing the amount of HN:F complex in the presence and absence of a test composition, one can detect whether a given test composition inhibits formation of an HN:F complex of a given paramyxovirus strain or type-homologous strains. It will be understood that it does not matter, from a practical standpoint, whether the inhibitor acts by preventing initial formation of the HN:F complex or by disrupting a complex after it is formed, since the measured result is a reduced amount of HN:F when inhibitor is present, compared to when it is absent. Therefore, the terms "inhibitor" and "inhibitor of HN:F complex formation" are not intended to imply any mechanism by which the amount of HN:F is reduced. Furthermore, it will be understood that a given inhibitor may be specific to type-homologous virus strains, or it may have a broader spectrum of activity.

Another consequence of the finding that an HN:F complex forms in infected cells or in cells cotransformed with type-homologous HN and F coding sequences of DNA is that the complex is a novel antigen. Novel antibodies directed against the HN:F complex can be raised. Such anti-HN:F antibodies can be polyclonal or monoclonal. Antibodies to HN:F inhibit the activity of HN:F in promoting cell fusion and intracellular virus transfer. Consequently, HN:F complexes form the basis of a novel type of subunit vaccine against type-homologous virus strains. HN:F can be used either alone or in combination with other viral antigens, such as HN and F, to generate protective antibodies to type-homologous virus infection. Labeled anti-HN:F antibody is also useful as a quantitative reagent for detecting, localizing, and measuring HN:F.

The finding that HN:F is only formed between type-homologous HN and F has provided a strategy for identifying an antiviral peptide. The strategy in essence involves mapping the peptide domains of HN and F which interact to form an HN:F complex and maintain its stability. Since HN and F of different type specificity do not form HN:F, it is possible to use chimeric HN or chimeric F proteins, between HN or F proteins, respectively, of different type specificity, to test the type specificity of the chimeras. By testing a series of such chimeras it has been possible to define the regions which do not contribute to type specificity in HN:F formation, and those regions which do contribute. The latter include those which interact in the HN:F complex. Oligopeptides comprising an amino acid sequence of a peptide region of HN or F that contributes to type specificity act as an inhibitor of HN:F formation. Such oligopeptides can be synthesized chemically or biologically (by transforming a cell with a DNA encoding the oligopeptide). Testing for the ability of a given peptide to inhibit HN:F formation is a straightforward application of the methods described herein for demonstrating the existence of HN:F. A direct test is one which measures HN:F, for example, by immunoprecipitation, while an indirect test is one which measures cell fusion caused by the presence of functional HN:F, for example, cell fusion, capping/cocapping analysis, or by cell-fusion-dependant reporter gene expression.

The experimental details are given in the Examples which show: (Example 1) that HN:F can be immunoprecipitated by antiserum to HN; (Example 2) that HN:F complexes are membrane-localized; (Example 3) that the HN and F proteins comigrate in cell membranes; that the quantity of HN:F formed in the presence or absence of divers test compositions forms the basis of a test for anti-paramyxovirus agents; (Example 4) that antibodies specifically directed to the HN:F complex can be raised; and (Example 5) that HN:F preparations provide the basis for an anti-paramyxovirus vaccine. Example 6 describes techniques for mapping peptide domains of HN or F that interact in HN:F formation. Many of the techniques and materials upon which the Examples are based are described below. Example 7 describes a series of type-chimeric HN peptides that define a region of HN required for type-homologous fusion. Example 8 describes a peptide corresponding to a region of F, and the activity of the peptide to inhibit cell fusion in type-homologous fashion.

The F-peptide described in Example 8 corresponds to a sequence of paramyxovirus F protein that include the heptad B repeat and amino acids lying between the heptad B repeat and the transmembrane domain. The peptide has been shown to inhibit cell fusion resulting from type-homologous paramyxovirus infection. The peptide has also been shown to inhibit virus spread from infected cells to non-infected cells. Both viral entry and spread of infection were inhibited. Peptides of the F-type disclosed exert their effects in infected animals or humans and are therefore useful as therapeutic agents to inhibit virus spread from infected to non-infected cells within the infected individual. Administration of the F-peptide can reduce the severity of symptoms, shorten the course of disease and allow time for the individual's immune system to mount an effective response. It is recognized that not all of the described region including the heptad B repeat and amino acids lying between the heptad B repeat the transmembrane domain are required for type-homologous binding or for inhibition of HN:F formation, virus entry into cells and cell-to-cell spread of infection. A minimum of about 5 amino acids within the described sequence can constitute a binding site with sufficient binding energy to display the observed type-homologous activity. More preferred will be a peptide of at least about 10 amino acids length. Peptides including an active core of 5 or 10 amino acids from the described sequence can be extended to include additional amino acid sequence outside the described sequence. Such extended peptides can also possess functional features of desired utility. Large numbers of candidate peptides are readily screened for the desired activity using, e.g. fusion-dependent reporter gene expression.

The foregoing general principles also apply to peptides corresponding to the HN type-homology region, a sequence of about 100 amino acids situated between the transmembrane domain and the C-termino and adjacent to the transmembrane domain. Peptides corresponding to that sequence, as well as certain sub-segments thereof as short as about 5 amino acids or preferably at least about 10 amino acids have the ability to disrupt or inhibit the formation of HN:F. That activity manifests itself as an ability to inhibit cell fusion, viral entry and virus spread from cell to cell. The shorter subsegments can be combined with segments of HN amino acid sequence outside the defined sequence to produce functional peptides having a desired utility.

It is well known that the function of a peptide can be reproduced by analog compounds and by model compounds that provide the same or approximate juxtaposition of reactive groups as the original peptide. Such analogs and model compounds can be generated by computer aided design, which begins with an analysis of the 3-dimensional conformation of the original peptide. However such analysis is not required since various combinatorial chemical syntheses are available for producing millions of candidate analogs which can be selected for activity by simple binding methods. Therefore analogs and model compounds having the activities described herein associated with inhibition of HN:F formation (inhibiting cell fusion, virus entry and cell-to-cell virus spread) are available to those ordinarily skilled in the art.

Viruses and Cells. PI2 and PI3 viruses were obtained from the Division of Research Resources, National Institutes of Health, Bethesda, Md. The viruses were grown on LLC-MK$_2$ cells as described previously (Hu et al., 1992). The vaccinia-T7 recombinant virus (WR strain) was obtained from Dr. Bernard Moss. HeLa-T4 and HeLa cells were purchased from the American Type Culture Collection (ATCC), Rockville, Md. Cells were grown in Dulbecco's modified Eagle's medium containing 10% defined/supplemented newborn calf serum (Hyclone Laboratories, Inc., Logan, Utah).

Recombinant Plasmids. PI2-F and HN cDNA genes were cloned in pGEM-3 and pGEM-3Zf(-) plasmids (Promega Biotech, Madison, Wis.), respectively, at the Sma I site as described previously (Hu et al., 1992). The P13 F and HN cDNA clones were kindly provided by Dr. Mark Galinski. These two genes were subcloned into pGEM plasmid vectors. The pGEM-4-SNF and pGME-4-SN HN cDNA clones were kindly provided by Dr. Laurent Roux. The SV5-F and -HN cDNA clones were kindly provided by Dr. Robert A. Lamb and were subcloned in pGEM plasmids. The PI1-HN cDNA gene was obtained from Dr. Yumiko Matsuoka and was subcloned in pGem-4.

Rabbit Antisera. Rabbit antisera against PI1 or PI3 viruses were produced as described previously (Hu et al., 1992). Rabbit antisera against PI2-HN and PI3-HN were generated as described by Ray and Compans (1987). Rabbit antiserum against Sendai virus was kindly provided by Dr. Laurent Roux. Rabbit antiserum against SV5 virus was kindly provided by Dr. Robert A. Lamb.

Infection and Transfection. Infection of cells with paramyxoviruses was performed as previously described (Hu et al., 1992). For the vaccinia-T7 expression system, confluent monolayers of cells grown in 35-mm dishes were infected with the vaccinia-T7 recombinant (Fuerst et al., 1986, supra) at a M.O.I. of 10 and incubated at 37° C. for 45 min. Cells were carefully washed with phosphate-buffered saline (PBS) 3 times and then transfected with 5 mg of plasmid DNA and 20 ml of cationic liposomes in 2 ml of Dulbecco's modified Eagle's medium. Cationic liposomes were prepared according to the procedure of Rose et al. (1991) BioTechniques 10:520–525: 2 mg of dimethyldiotadecylammonium bromide (DDAB) (SIGMA, St. Louis, Mo.) was dissolved in 5 mg of 10 mg/ml dioleoyl-L-a-phosphatidylethanolamine (PtdEtn) (SIGMA), dried in a speed vacuum concentrator and resuspended in 5 ml of sterile distilled water by sonication. Dulbecco's modified Eagle's medium with or without 5% newborn calf serum was added after cells were incubated with the transfection mixture at 37° C. for 5 h. Immunoprecipitation assays were performed 12 to 16 h posttransfection.

Radiolabeling and Immunoprecipitation. Twelve hours post-transfection, cells were starved in Dulbecco's modified Eagle's medium lacking methionine and cysteine for 15 min and labeled with 60 mCi of [$^{35}$S]methionine per 35-mm dish for 1 h at 37° C. Immunoprecipitation was performed as described previously (Hu et al., 1992) and the radiolabeled polypeptides were analyzed by SDS-polyacrylamide gel electrophoresis (SDS-PAGE).

Cross-linking. Cross-linking was carried out by a modification of the procedure described by Hamada and Tsuruo (1987). Transfected cells were labeled with [$^{35}$S]-methionine as described above. Cells were incubated with 1 mM dithiobissuccinimidylpropionate (DSP, dissolved in PBS) (Pierce, Rockford, Ill.) on ice for 30 min, and then cross-linkers quenched with Dulbecco's modified Eagle's medium. Cells were lysed with mild lysis buffer (10 mM lauryl maltoside, 100 mM NaCl, 50 mM Hepes, pH 7.3) and the viral proteins were then immunoprecipitated as described above.

Biotinylation Assay. Biotinylation of cell surface proteins was performed as described by [Lisanti et al. (1989) J. Cell. Biol. 109:2117–2127]. Briefly, transfected cells were labeled with 100 mCi of [$^{35}$S]-methionine/35-mm dish 10 to 12 hr posttransfection, washed with cold PBS/CM (0.1 mM CaCl$_2$, 1 mM MgCl$_2$ in PBS-D) three times and agitated with PBS/CM on ice for 30 min. After addition of NHS-SS-Biotin (Pierce, Rockford, Ill.) at a concentration of 0.5 mg/ml, cells were incubated on ice with agitation for 15 to 30 min. Cells were then lysed with lysis buffer and antibody was added. After addition of 10 ml of 50% protein A agarose beads and incubation at 4° C. for 2 h, cell lysates were washed with the lysis buffer and 10 ml of 10% SDS was added followed by boiling for 5 min. Supernatants were separated from agarose beads by addition of lysis buffer and centrifugation in a microcentrifuge. Ten ml of 50% Streptavidin agarose beads were added to the supernatant followed by incubation at 4° C. for 2 h. Beads were then washed and boiled, and biotinylated proteins were analyzed by 10% SDS-PAGE.

Capping and Cocapping Assays. HeLa cells were grown in 100-mm cell culture dishes in Dulbecco's modified Eagle's medium with 10% newborn calf serum. Antibody-induced capping was performed as described by Joseph and Oldstone (1974) J. Immunol. 113:1205–1209. Briefly, confluent monolayers of cells were infected with PI1 or PI3 virus at a M.O.I. of 5 and incubated at 37° C. for 1 h. Virus-infected cells were then washed with warm PBS-deficient (PBS-D, PBS lacking Mg$^{++}$ and Ca$^{++}$) three times and suspended with 50 mM EDTA at room temperature. Suspended cells were washed and transferred to snaptop tubes in Joklik's medium containing 2% newborn calf serum and incubated at 37° C. for 16 to 20 hr. After cells were washed with ice-cold PBS-D and pelleted by centrifugation at 1,000 rpm, primary antibody to the viral antigen was added followed by incubation on ice for 30 min. Cells were then washed with ice-cold PBS-D and divided into two aliquots. After the secondary antibody conjugated with fluorescein isothiocyanate (FITC) was added, the two aliquots of cells were incubated at 37° C. or 0° C., respectively, for 30 to 60 min. Cells were finally fixed in 1% paraformaldehyde and resuspended in 200 ml of PBS-D for fluorescence microscopy.

Cocapping analysis was carried out by adding primary antibody to the second antigen and secondary antibody conjugated with rhodamine isothiocyanate (RITC) with each incubation interval for 30 min on ice. Cells were washed with cold PBS-D and pelleted at 1,000 rpm after each incubation. Fluorescence microscopy was performed by using two different fluorescence filters for FITC and RITC, respectively.

Quantitative Fusion Assay. To quantitate the cell fusion activity, the fusion dependent reporter gene activation method which was reported by Nussbaum et al. (1994) J. Virol. 58:5411–5422 was employed with modification [Yao, Q. et al. (1995) J. Virol. 69:7045–7053]. Briefly, for HN:F induced fusion, HeLa-T4 cells were infected with the recombinant vaccinia virus vTF7-3 and transfected with the SN-F plasmid together with the HN or chimeric HN recombinant plasmids. Another population of the HeLa-T4 cells was infected with wild type vaccinia virus (IHD-J) and transfected with the plasmid pG1NT7β-gal which contains the β-galactosidase gene under the control of the T7 promoter (25). After 14 h incubation, the cells were mixed in the presence of trypsin (0.1 μg/ml, type XIII, Sigma Chemicals) and further incubated for 5 h. Cell fusion provides transmission of T7 RNA polymerase from vTF7-3 infected cell to the pG1NT7β-gal transfected cells, enabled expression of the β-galactosidase. The produced β-galactosidase was measured by absorbance at 570 nm after addition of CPRG substrate. Fusion activity was expressed as a percentage of the amount of β-galactosidase production in the cells transfected with SN-F and wild type SN-HN genes. The use of a fusion-dependent reporter gene expression assay permits rapid and simple screening of large numbers of candidate compounds, including peptides, peptide analogs and model compounds for their ability to inhibit cell fusion, hence to inhibit HN:F formation.

Hemadsorption Activity. Transfected HeLa-T4 cells were incubated with 0.5% guinea pig erythrocytes for 30 min at 4° C. and unbound cells were removed by extensive washing. The cells were observed under the microscope. The bound red blood cells were lysed with 50 mM ammonium chloride and the eluted hemoglobin concentration (O.D. at 459 nm) was determined as a measure of hemadsorption activity [Morrison, T. G. et al. (1989), Virology 171:10–17].

Cell Fusion Assays. For virus-induced fusion monolayer of HeLa-T4 cells were infected with PI2, PI3 or SV5 at m.o.i. of 0.1. After the virus was absorbed at 37° C. for 1 h, the inoculum was removed and DMEM with 2.5% of FBS was added to the well with or without addition of serial dilutions of each peptide. For vaccinia expression studies, confluent monolayers of cells were infected with vTF7.3 at a m.o.i. of 10, and incubated at 37° C. for 1 h. After washing out the inoculum, cells were then transfected with 2 μg of F and HN plasmids DNA with lipofectin (GIBCO-BRL, Gaithersburg, Md.) in 0.5 ml of DMEM. After 24 h (for virus infected cells) or 18 h (for transfected cells) of incubation at 37° C. in a 5% CO2 atmosphere, the formation of syncytia was compared with the infected or transfected cell control containing no additional peptide. Cell fusion was measured by polykaryon formation and expressed as (number of nuclei in polykaryons/number of total nuclei)×100. Cells were counted in five different fields under a light microscope. Dose-response curves were also generated using this method.

EXAMPLE 1

Immunoprecipitation of HN:F. The existence of an HN:F complex was tested by cross-linking and coprecipitation experiments.

HeLa-T4 cells were transfected with PI2-F and HN (see FIG. 1, lanes 1 to 3); PI2-F (FIG. 1, lanes 4 and 5); PI2-HN (FIG. 1, lanes 6 and 7) or infected with VV-T7 (FIG. 1, lanes 8 and 9). Cells were labeled [$^{35}$S]-methionine for 1 hr at 37° C. 12 hr posttransfection. Cross-linking was performed by incubating cells with 5 mM dithiobissuccinimidyl-propionate (DPS) on ice for 30 min (FIG. 1, lanes 3, 5, 7, and 9). Cells were then lysed with lysis buffer (10 mM lauryl maltoside, 100 mM NaCl, 50 mM hepes, pH 7.3) and immunoprecipitated with rabbit anti-PI2 virus antiserum (lane 1) and rabbit anti-PI2 HN antiserum (lanes 2 to 9).

After treatment with the cross-linker DSP, the PI2-F and -HN proteins were found to be coprecipitated by rabbit antiserum to PI2-HN (FIG. 1, lane 3). In the absence of DSP, anti-PI2-HN antiserum also coprecipitated the PI2-F protein (FIG. 1, lane 2), suggesting that the F and HN proteins are strongly associated with each other. Under the same conditions, no F protein was found to be precipitated in the absence of HN (FIG. 1, lanes 4 to 9) and no nonspecific proteins were coprecipitated in the presence of the crosslinker DSP (FIG. 1, lanes 5, 7, and 9). Similar results were obtained under conditions using strong lysis buffer such as RIPA buffer.

EXAMPLE 2

Figure 2:
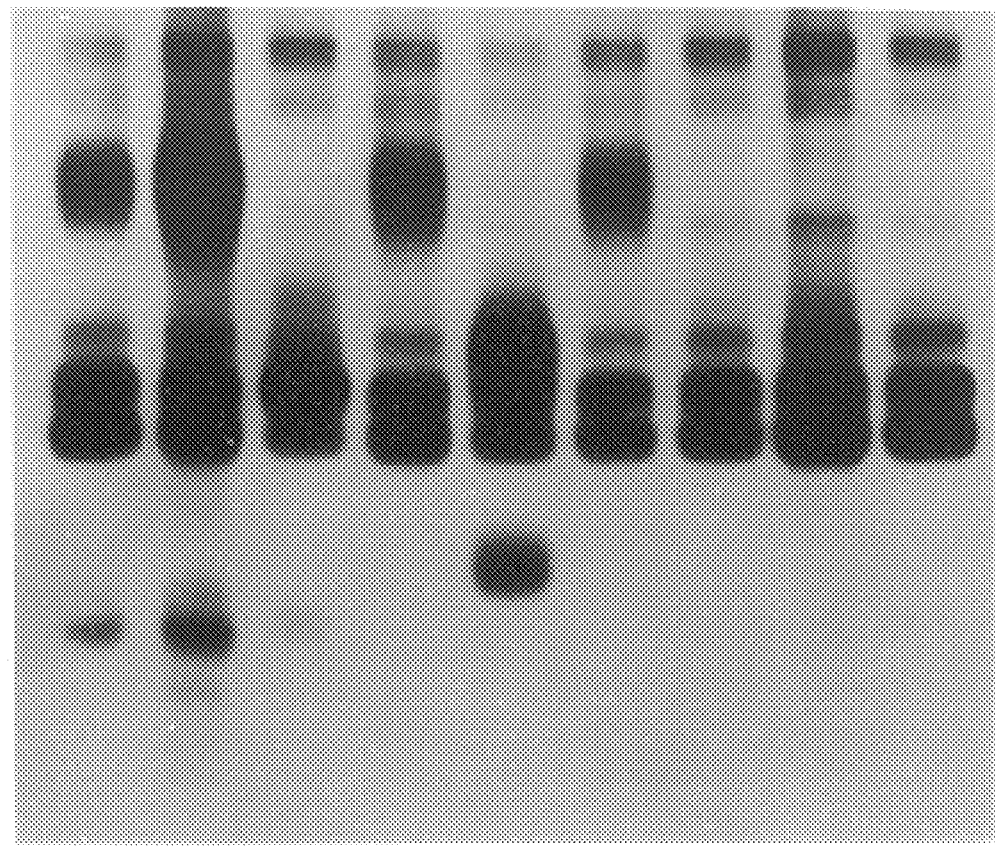
FIG. 2 shows SDS-PAGE separations of labeled proteins in the biotinylation and coprecipitation experiment described in Example 2. The positions of $F_1$ and HN are indicated at the left; lane numbers at the top of each lane.

Cell-surface location of HN:F complex. To investigate the interactions of the F and HN proteins on the cell surface, a biotinylation assay was employed to label the proteins on the cell surface. Results are shown in FIG. 2. HeLa-T4 cells were cotransfected with PI2-F and PI2-HN (lanes 1 and 2), SN F and SN HN (lane 3), SN F and PI2-HN (lane 4), SV5-F and SV5-HN (lane 5), SV5-F and PI2-HN (lane 6), or transfected with PI2-F (lane 7), SN F (lane 8) of SV5-F (lane 9). At 12 hr posttransfection cells were labeled with [$^{35}$S]-methionine for 3 hr at 37° C., surface proteins were biotinylated with NHS-SS-Biotin and then the biotinylated proteins were immunoprecipitated with rabbit anti-PI2 virus antiserum (lane 1), rabbit anti-PI2-HN antiserum (lanes 2, 4, 6 to 9), rabbit anti-Sendai virus antiserum (lane 3), or rabbit anti-SV5 antiserum (lane 5). One μg/ml trypsin was added to SN F-transfected cell medium during the labeling. Biotinlyated proteins were finally precipitated with Streptavidin agarose beads and analyzed by SDS-PAGE.

As shown in FIG. 2, the homologous F protein, PI2-F, was found to be coprecipitated by anti-PI2-HN antiserum (lane 2), whereas heterologous F proteins, SN F (lane 4) or SV5-F (lane 6), were expressed on cell surfaces but were not coprecipitated when coexpressed with PI2-HN and precipitated by PI2-HN antiserum. These results indicate that the PI2-F and HN proteins are physically associated with each other on cell surfaces, whereas heterologous combinations of F and HN do not show a similar association. Thus, the physical association of F and HN as revealed by the coprecipitation experiments parallels their functional interaction in the induction of cell fusion.

EXAMPLE 3

Figure 3A:
FIGS. 3A–3C are micrograph showing capping and cocapping of F and HN proteins as described in Example 3. The results are shown in double exposure with the field moved slightly to show: A) a capped cell (left) and an uncapped cell (right); B) FITC fluorescence used to label HN (right) and RITC fluorescence used to label F (left) on the same capped cell; C) FITC fluorescence used to label PI2 HN under capping conditions (left) and RITC fluorescence used to label PI3 F under noncapping conditions (right), on the same cell.
Figure 3B:

Type-homologous F and HN Glycoproteins were found to cocap on the cell surface. To further study the interactions of the F and HN proteins on the cell membrane, capping and cocapping assays were performed in HeLa cells which were infected with PI3 virus or doubly-infected with PI2 and PI3 viruses. As described in "Capping and Cocapping Assays," supra, two aliquots of HeLa cells infected with PI3 virus were incubated with rabbit anti-PI3-HN antiserum at 0° C. for 30 min followed by incubation with FITC-conjugated secondary antibody (goat antirabbit IgG) at 37° C. or 0° C. for 30 min. The PI3-HN proteins were found to redistribute to form a unipolar cap when cells were incubated at 37° C. (FIG. 3A), whereas cells incubated at 0° C. showed random distribution of the PI3-HN proteins on the cell surface (data not shown). If under conditions facilitating capping (at 37° C.) of HN, the F proteins also form a cap at the same position (cocapping) on the cell surface, this would indicate that these two proteins are physically associated with each other since they move together laterally. Cocapping was therefore examined by double staining with FITC-labeling for the HN proteins and RITC-labeling for the F proteins, respectively. After cells were infected with PI3 virus for 12 to 16 hr, cells were incubated with rabbit anti-PI3-HN antiserum (at 0° C.) and FITC-conjugated goat antirabbit IgG (at 37° C.) for 30 min and 45 min, respectively, followed by incubation for 30 min with monoclonal antibody to PI3-F (at 0° C.) and RITC-conjugated goat antimouse IgG (at 0° C.). As indicated by the double exposure in FIG. 3B, on the surface of the doubly-stained cells the two membrane proteins were redistributed to form a unipolar cap in the same position; the RITC-stained PI3-F proteins were found to overlap the FITC-stained PI3-HN proteins.

Figure 3C:
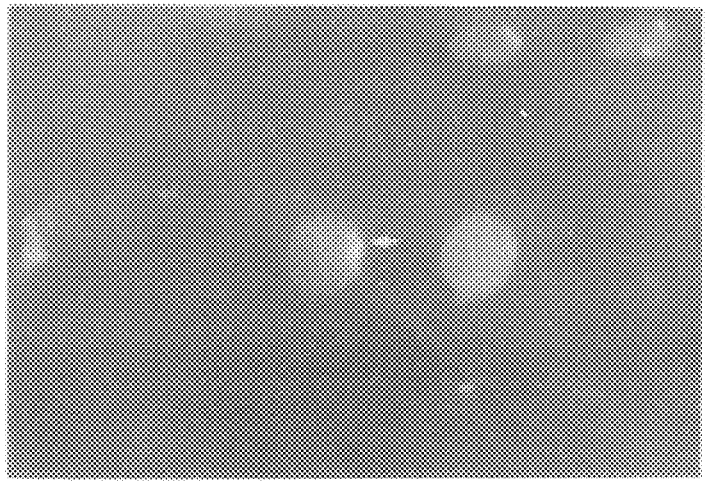

We also investigated the physical relationship between heterologous combinations of F and HN proteins on the cell surface by the capping assay. PI2 and PI3 virus-coinfected cells were incubated with rabbit anti-PI2-HN antiserum for 30 min at 0° C. and subsequently with FITC-conjugated goat antirabbit IgG for 45 min at 37° C. Then, cells were incubated with monoclonal antibody against PI3-F and RITC-conjugated goat antimouse IgG at 0° C. for 30 min, respectively. As shown in FIG. 3C, FITC-stained PI2-HN formed a cap while RITC-stained PI3-F remained uniformly distributed on the cell surface (shifted to the right in the double exposure). Coinfected cells which were doubly stained but incubated at 4° C. did not show capping (data not shown). These results further indicate that F and HN proteins of the same virus type are physically associated with each other and they can laterally move together on the cell surface under certain conditions, whereas heterologous F and HN proteins fail to show a similar association.

EXAMPLE 4

Specific antibodies to HN:F. Purified, partially purified or crude preparations of HN:F are used to immunize an animal or human to prepare polyclonal antibodies specific to HN:F complexes. Such preparations are also used to select for monoclonal antibodies specific for HN:F. Antibodies concurrently raised against contaminants in the HN:F preparation used for immunization are removed by standard antibody clearance techniques known in the art. Antibodies raised against a crude HN:F preparation from transfected HeLa-T4 membranes are cleared by reaction with similarly prepared membranes from cells transformed with vector only. Antibodies specific to the HN and F moieties only are similarly cleared by reaction with purified HN and F. [Standard techniques of immunization, antibody purification, and monoclonal antibody preparation are given in Harlow, E. and Lane, D., *Antibodies, A Laboratory Manual*, Cold Spring Harbor Laboratory, Cold Spring Harbor, N.Y. (1988)].

HN:F complexes have been shown herein to be stable to cell lysis conditions (Examples 1 and 2) which employ a mild detergent, lauryl maltoside. Adaptations of techniques previously employed for purifying HN and F [Ray, R. and Compans, R. (1987) *J. Ge. Virol.* 68:409–418] are applied to initial stages of purifying HN:F complex. Affinity chromatography using antibody as the affinity ligand is not employed, however, because the conditions used for elution disrupt the HN:F complex. The whole cell lysates of transfected cells can be used as a crude HN:F preparation, after dialysis to remove detergent and resuspension of membrane components. Alternatively, purified virus particles can be used as a source of HN:F. HN:F is further solubilized with octyl-D-glucoside or cholate and reconstituted into lipid vesicles [Ray, R. and Compans, R. (1987): Compans et al., U.S. Pat. No. 4,790,987]. Contaminating host cell proteins are removed by immunoprecipitation using antibodies to nontransformed host cells. Further purification can be carried out by affinity chromatography using a natural ligand of HN:F, e.g. sialic acid, as the affinity ligand. Elution can then be carried out under mild conditions such as a salt gradient that do not disrupt HN:F.

Immunization by HN:F, either alone or in combination with uncompleted HN and F, provides protective immunity against infection by type-homologous virus. It will be understood that protection need not be complete to be of value. Protection is provided if, by any clinical signs or laboratory measurement related to disease severity, the normal course of disease in an infected animal or human patient is ameliorated. Indicia of protection include, but are not limited to, reduction in severity or duration of symptoms, reduction of virus titre from lungs, trachea or other tissues, reduction in histopathology, and the like. The use of HN:F as an immunizing antigen leads to production of antibodies to HN, F and HN:F. Since the latter is directly involved in tissue pathology and virus spread, antibodies against HN:F inhibit these activities and thereby contribute to and enhance the immunity conferred by HN and F as separate components.

Immunization by HN:F is carried out by techniques known and previously applied successfully in the art. In general, an immunologically effective amount of HN:F is administered to the animal or human to be immunized, either systemically or preferably intranasally. An immunologically effective amount is that amount sufficient to elicit an antibody response in the animal or human subject. For HN:F, an immunologically effective amount is comparable to the amounts already known for securing protection using uncomplexed HN and F.

A vaccine against a paramyxovirus strain contains as its principal ingredient HN:F in an immunologically effective amount, together with a physiologically acceptable carrier in which HN:F is either suspended or dissolved. Optionally, the vaccine can also include lipid to incorporate HN:F in lipid vesicles and an adjuvant to enhance intensity of the immune response. By using HN:F of a single virus type, protection is limited to infection by type-homologous viruses. Multivalent vaccines are prepared by incorporating HN:F of more than one virus type. By incorporating HN:F of PI1, PI2, and PI3, for example, a vaccine protective against all three virus types is produced. In addition, noncomplexed HN and F of one or more of the types can be included.

EXAMPLE 5

Vaccine Based on Anti-HN:F Antibodies. Protective immunity conferred by vaccines comprising HN, F, or both as the primary antigens, has been demonstrated for several paramyxovirus strains [Compans et al., U.S. Pat. No. 4,790, 987; Ray, R. et al. (1985) *J. Infect. Dis.* 152:1219–1230; Ray, R. et al. (1988) *J. Virol.* 62:783–787; Ray, R. et al. (1988) *J. Infect. Dis.* 157:648–654; Ray, R. et al. (1990) *J. Infect. Dis.* 162:746–749; Taylor, J. et al. (1991) *J. Virol.* 65:4263–4274]. These studies have further established that combined administration of HN and F provides greater protection than immunization with either HN or F singly [Ray et al. (1988) *J. Virol.*]. Immunization by intranasal administration of the antigens provides greater protection than systemic administration, suggesting that the more significant immunity is IgA-mediated [Ray et al. (1988) *J. Infect. Dis.*]. The immunity conferred is type-specific, or at least type-homologous-specific [Ray et al. (1990), supra]. In studies of children infected with PI3, the appearance of antibodies to HN and F correlated with protection from infection [Kasel, J. A. et al. (1984) *J. Virol.* 52:828–832].

Therefore, the results of successful immunization of animals render similar results predictable in the case of human immunization.

EXAMPLE 6

Peptide Mapping and Method of Selecting Antiviral Peptides. In order to identify the peptide domains of HN and F, which are critical for type-specific HN:F formation, a series of chimeric HN (or F) proteins is constructed. A chimeric HN protein is constructed having one or more segments obtained from PI2-HN and remaining segment(s) obtained from SV5-HN.

Because the PI2 and SV5-HN genes show a high level of sequence identity [Kawano et al., (1990) *Virology* 174:308–313; Hiebert et al., (1985) *J. Virol.* 54:1–6], initial studies are focused on these genes. Similar studies were also carried out with PI3 and SN as detailed in Example 7. To identify the regions of the HN protein that participate in type-specific fusion complex formation with the F Protein, a series of chimeric HN genes are constructed and expressed (see FIG. 4). This approach offers advantages over the alternative approach of introducing deletions into glycoprotein genes, because it seems less likely that one would encounter possible problems of incorrect folding with the chimeric molecules.

Sequences of the PI2-HN gene are sequentially replaced with sequences of the same regions from the SV5-HN gene. The PI2 and SV5-HN genes contain a number of appropriate single restriction sites to produce convenient DNA fragments (FIG. 5). The disulfide bonds in the two genes are conserved, so the chimeric proteins are considered to have similar folding properties.

Since in most cases the nucleotide sequence of one HN gene does not contain the same restriction site as the HN gene from the other virus, DNA fragments are synthesized by PCR with Pfu DNA polymerase (Stratagene, La Jolla, Calif.) that possesses proofreading activity resulting in a 12-fold increase in fidelity of DNA synthesis over Taq DNA polymerase. The oligonucleotide primers for PCR are designed to contain restriction sites for subsequent ligation. After purification by means of a "Geneclean II kit" (Bio 101, La Jolla, Calif.) DNA fragments from PI2 or SV5-HN genes are used to replace the corresponding fragments of the heterologous HN genes in the pGEM3 vector. The restriction endonuclease maps and DNA sequence of junction regions are determined to confirm the structures of chimeric genes.

HeLa T4 cells are used for protein expression studies and fusion assays since they are resistant to vaccinia-induced cytopathic effects [Matsuoka et al., (1988) *Virus Res.* 16:107–113]. Cells infected with the vaccinia virus-T7 recombinant (vv-T7) [Fuerst et al., (1986) *Proc. Nat. Acad. Sci. USA* 83:8122–8126] at a multiplicity of infection of 10 are transfected with 5–10 μg of plasmid DNAs, using lipofectin (TM GIBCO-BRL, Gaithersburg, Md.). After 12 to 20 h incubation at 37° C., cells are analyzed for protein expression by radiolabeling and immunoprecipitation. Cells are labeled with [$^{35}$S] methionine (100 μCi/ml) in methionine-free medium at appropriate time points post-transfection. Cells are lysed with cell lysis buffer (50 mM Tris-HCl, pH 7.5, 0.15 M NaCl, 1% Triton X-100, 0.1 SDS, 20 mM EDTA) and then analyzed by SDS-PAGE [Laemmli, (1970) *Nature* 227:680–685]. To ensure that each expressed protein is transport-competent, cell surface expression is monitored by surface immunofluorescence staining. Cells are grown on glass coverslips and vv-T7 infection and plasmid transfection are performed as described above. At appropriate time points, cells are washed with PBS, fixed with 1% paraformaldehyde in PBS for 5 min at room temperature, and examined by indirect immunofluorescence using polyclonal antibodies against PI2 or SV5-HN proteins and an appropriate fluorescent conjugate. In addition, the biological activity of the chimeric proteins is evaluated by hemadsorption and neuramindase assays. After ensuring that chimeric HN proteins are expressed and transported to the cell surface, they are then coexpressed with the wild-type PI2 or SV5-F proteins to examine whether the fusion-promotion activity is altered. To study the influence of HN on membrane fusion, HeLa T4 cells are infected with vaccinia-T7 recombinant [Fuerst et al., (1986), supra] and later are cotransfected with plasmid DNAs encoding the wild type F protein from PI2 or SV5 and chimeric or mutant HN protein genes using lipofectin. At 18 hr posttransfection the number of nuclei in 50 fused cells and the number of syncytia in 10 different fields of view are counted to determine the average size of syncytia and the frequency of cell fusion. Values obtained after transfection of the vector alone are subtracted. After the initial regions of HN important for interaction with F proteins are determined, chimerics in which smaller regions are exchanged are constructed and tested to further delineate the regions which are critical for fusion.

By analyzing which chimeric HNs form HN:F complex with PI2-F or SV5-F, one is able to map the region or regions within the HN amino acid sequence that contribute to type specificity, and to identify the sequence domains that participate in binding between HN and F.

To investigate the interactions of the F and HN on the cell surface, a biotinylation assay is employed to label the proteins on the cell surface [Lisanti et al., (1989), supra]. Cells are transfected with chimeric HN and either PI2 or SV5-F genes, metabolically labeled with $^{35}$S-methionine. Cell surface proteins are biotinylated with NHS-SS-Biotin (Pierce, Rockford, Ill.). After cells are lysed, samples are immunoprecipitated with specific antibodies to HN or F solubilized and then precipitated with streptavidin agarose beads (Pierce, Rockford, Ill.) to isolate the cell surface glycoproteins followed by SDS-PAGE analysis. One will thus determine whether the glycoproteins on cell surfaces are coprecipitated by antibody to one or the other glycoprotein. The results are compared with or without cross-linking. These results should indicate which chimeric HN proteins form complexes with either PI2 or SV5-F proteins.

The association of the two proteins on the cell surface can also be examined by a capping assay. It has been shown that viral glycoproteins can redistribute on the cell surface in response to multivalent antibody [Joseph and Oldstone, (1974) *J. Immunol.* 113:1205–1209]. If F and HN are closely associated, both molecules form a unipolar cap in the same position after incubation with specific antibody to one or the other protein. For this experiment, one uses antibodies produced in different animal species in order to distinguish the two proteins with appropriate conjugated second antibodies. The F and HN proteins are HeLa cells and at an appropriate time point cells are suspended, incubated with rabbit anti-HN antibody for 30 min at 0° C. and subsequently with FITC-conjugated goat antirabbit IgG for 45 min at 37° C. During the incubation period at 37° C., HN is redistributed into a cap structure on a significant fraction of cells. Cells are then incubated with mouse MAb against F and RITC-conjugated goat antimouse IgG at 0° C. for 30 min and individual cells are examined for fluorescein and rhodamine fluorescence to determine whether the F protein has redistributed to the same position. Similar experiments are using SV5-F instead of PI2-F. This provides an alternative approach for detecting the interaction of HN and F on cell surfaces.

Figure 6:
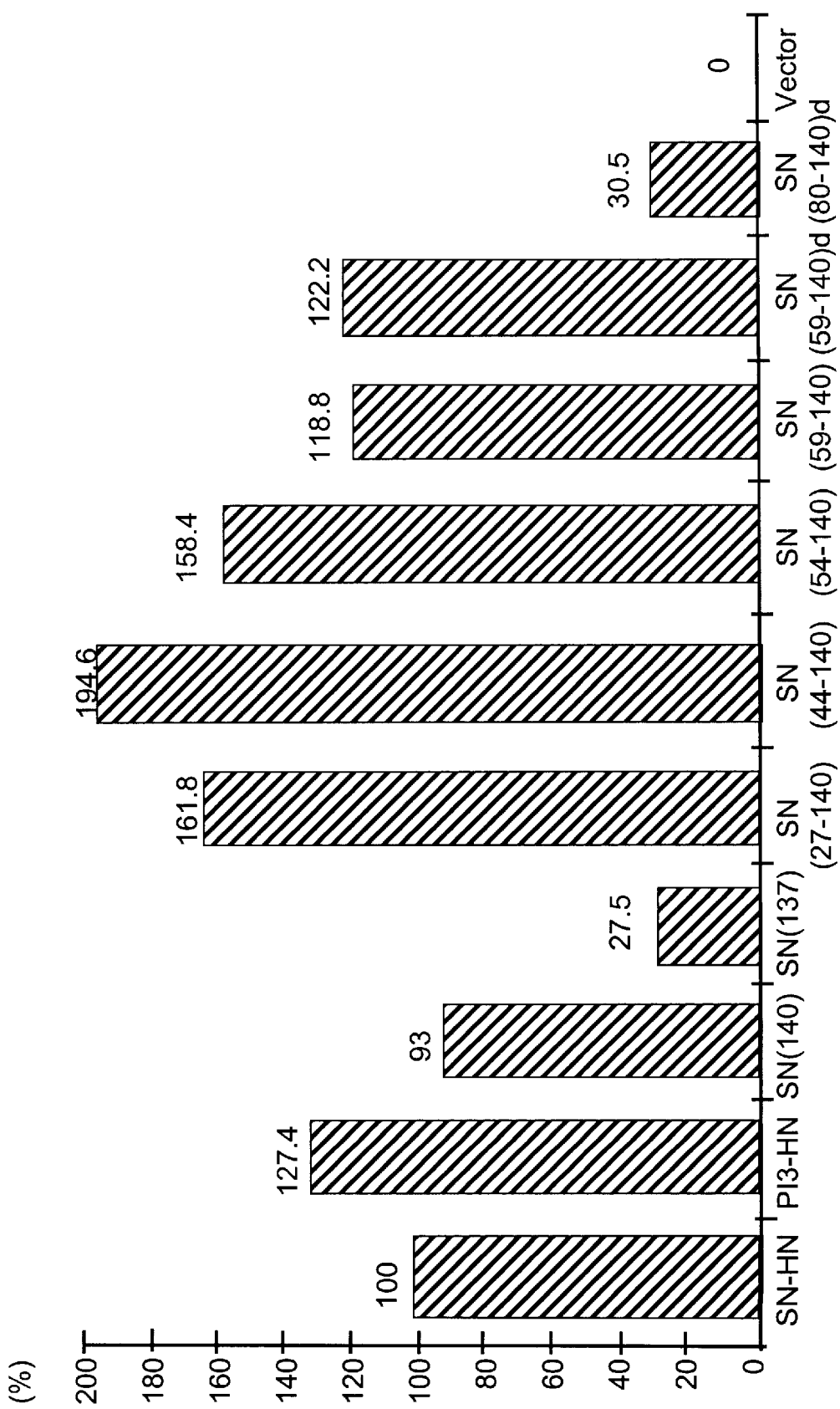
FIG. 6 Hemadsorption activities of chimeric HN proteins. The transfected cells were incubated with a 5% suspension of guinea pig erythrocytes for 30 min at 4° C. After removing unbound cells by washing, the cells were observed using an inverted microscope. The bound red blood cells were lysed with ammonium chloride and the absorbance was measured at 549 nm. The data are expressed as a percentage of released hemoglobin from SN-HN expressed cells.

In order to map the domains of the F protein that interact with the HN protein, chimeric genes between PI2 and SV5-F genes are similarly constructed and expressed. Sequences of one of the F genes are progressively replaced with the sequences of the same regions of the other F gene (FIG. 6). These studies complement the proposed studies of the HN gene.

The chimeric F proteins are coexpressed with HN from PI2 or SV5 wild type viruses to examine whether their fusogenicity is altered. Once the area(s) important for interaction with HN are determined, chimerics with smaller domains are constructed and further tested. Regions with clustered amino acid changes related with fusion activity found in previous studies are focused on first. Site specific mutagenesis is used to precisely define the changes in particular amino acids involved in F-HN interaction.

Site-directed mutagenesis studies. After localization of the fusion-promotion region of PI2 and SV5-HN proteins, the next step is to determine the precise amino acid residues involved in interaction with the F protein for formation of an active fusion complex. After alignment, the amino acid sequences of HN proteins from the fusion promotion regions of PI2 and SV5 are compared and specific amino acids that differ between PI2 and SV5-HN proteins will be identified. For example, there are 3 short regions of amino acids inside the first 50 amino acid residues of the ectodomain that are similar between SN and PI1-HN and different for PI2 and SV5-HN. There are single cleavage sites for PstI, BglI and SspI restriction endonucleases near these regions of the SV5-HN gene so the introduction of point mutations into SV5-HN gene is facilitated.

To study the role of individual amino acid residues in fusion complex formation, site-specific mutagenesis by polymerase chain reaction (PCR) is used. Synthetic oligonucleotide primers for Pfu DNA polymerase (Stratagene, La Jolla, Calif.) are designed and synthesized (Novosibirsk Institute of Bioorganic Chemistry, Russia) to incorporate appropriate restriction sites as well as point mutations in primers used to amplify DNA fragments. Following PCR, the amplified fragments are cleaved by treatment with appropriate restriction endonucleases, and used to replace the corresponding segment of HN in a plasmid vector. Double mutants are generated from the first mutant by the same approach. Triple mutants are generated from the double mutant, and so on [McGinnes et al., (1993) *Virology* 196:101–110]. Thus, SV5 sequences are progressively replaced with PI2 sequences or vice versa. After sequencing to confirm the presence of the desired mutation(s), mutated HN genes are expressed from pGEM3 vectors transfected into vv-T7-infected HeLa T4 cells.

To determine the effect of such mutation(s) on the interaction with F protein, HeLa T4 cells are cotransfected with mutant HN and wild-type F genes of SVS or PI2 and the level of syncytia formation is quantitated in comparison with wild-type HN protein expression. Interaction of F and HN proteins to form complexes is evaluated by immune precipitation and cocapping as described above.

Fusion inhibition by synthetic peptides from fusion promotion regions. Peptides from regions of PI2-HN involved in membrane fusion are synthesized, purified by HPLC, and their solubility determined. When the interacting domains are present on the external surfaces of the cell, addition of peptides to the culture medium after transfection with PI2-F and HN genes results in competitive inhibition of F-HN interaction and membrane fusion. To assess the effect of peptides from the fusion-promotion region on F and HN interaction, synthetic peptides (0.1–200 μg/ml) are added to culture media after transfection with F and HN genes. Determination of the fusion frequency and the average size of giant cells are done as described above. When the interactions occur between intracellular portions of the F and HN molecules, one can prepare derivatized peptides to enhance peptide permeability.

The penetration of virus particles into cells also involves a membrane fusion process which is similar to the cell-to-cell fusion occurring later during virus infection. Thus, an inhibitor which prevents cell fusion also prevents virus replication. To measure inhibition of virus replication, peptide inhibitors which prevent fusion are incorporated at various concentrations into the agar overlay of plaque assays for PI2 virus on monolayers of Vero cells [Ray et al., (1989) *Virus Res.* 12:169–180]. The stage of infection at which inhibitors act is determined by addition of the inhibitors at various times postinfection during a single cycle of virus growth in LLC MK2 cells. Similar approaches are employed for inhibitors targeted to SV5 proteins.

To measure directly that synthetic peptides prevent the formation of complexes between F and HN, one examines the effect of peptides on formation of complexes assayed by immune precipitation or cocapping experiments as described above.

Studies with other paramyxoviruses. The steps set forth above focus on parainfluenza virus type 2 and SV5 because SV5 is the virus most closely related to PI2. However, it will be understood that one can extend this approach to other paramyxoviruses. In particular, human parainfluenza virus types 1 and 3 and respiratory syncytial virus (RSV) are important causes of respiratory infection, and new approaches for their control are of great importance.

EXAMPLE 7

Construction of the chimeric HN plasmids. All of the chimeric HN plasmids encoding various parts of the SN-HN and PI3-HN genes used in this study were generated by using the overlapping polymerase chain reaction (PCR) technique [Ho, S. N., et al. (1989) *Gene* 77:51–59; Horton, R. M. et al. (1989) *Gene* 77:61–68; Yao, Q. et al. (1995) *J. Virol.* 69:7045–7053]. See Table 1. For construction of the first chimeric plasmid, SN(140), a DNA fragment of SN-HN was amplified by PCR using synthetic oligonucleotide primer #5 (SEQ ID NO:1) (SN-HN5'EcoRI) and primer #7 (SEQ ID NO:2) with SN-HN plasmid as template, and the DNA fragment of PI3-HN was amplified with primer #8 (SEQ ID NO:3) and #6 (SEQ ID NO:4) (PI3-HNnN3'BamHI) with PI3-HN plasmid as template. The resulting DNA fragments had been designed to overlap at the 3' end of the SN-HN fragment and the 5' end of the PI3-HNM fragment. In the subsequent PCR, the two DNA fragments were used in a 5 cycle-reaction without primers and an additional 25 cycle-reaction with the primers #5 (SEQ ID NO:1) and #6 (SEQ ID NO:4). The final PCR products were digested with Eco RI and Bam HI and subcloned into the pGEM-3 vector which had

TABLE 1

| | 5' primer | overlapping chimeric primer | 3' primer |
|---|---|---|---|
| SN(140) | #5(SN-HN5'EcoRI) | #8  5'-CAGCTCTGTGAGAGT-AGAATAACACATGATGTGGGC-3' | #6 (PI3-HN3'BamHI) |
| | 5'-TACGAATTCATCATGGATGGTGATAGGGGCA-3' | #7  3'-GAGTGAGTCGAGACACTCTCA-TCTTATTGTGTACTA-5' | 3'-TAAGGTTTTCGACGTCAATTCCTAGGCAG-5' |
| SN(137) | #5(SN-HN5'EcoRI) | #15  5'-GAGCTCACTCAGCTC-CCTCCACAAAGAATAACACAT-3' | #16 (PI3-HNKpnI) |
| | | #14  3'-GTCTGTTCTCGAGTGAGTCGAG-GGAGGTGTTTCTTA-5' | 3'-GTCTGAACCATGGACTGAAT-5' |
| SN(27-140) | #27(PI3-HN5'EcoRI) | #25  5'-TCATGGCAAC-TGGGAGAGGTCAAGTAAAGT-3' | #16 (PI3-HNKpnI) |
| | 5'-CTCGAATTCGAGATGGAATACTGGAAGCAC-3' | #26  3'-GGTACCGATGAGTACCGTTG-ACCCTCTCCA-5' | |
| SN(44-140) | #27(PI3-HN5'EcoRI) | #31  5'-CCTGGTGTTA-CAGTGGGCTTTTGTCAATTGC-3' | #16 (PI3-HNKpnI) |
| | | #32  3'-CCTGTTATTAGGACCACAAT-GTCACCCGA-5' | |
| SN(54-140) | #27(PI3-HN5'EcoRI) | #39  5'-AGTGCTAATT-ATCTGTATCATAATTTCTGC-3' | #16 (PI3-HNKpnI) |
| | | #40  3'-AGAAGTAGTATCACGATTAA-TAGACATAGT-5' | |
| SN(59-140) | #27(PI3-HN5'EcoRI) | #29  5'-CATCAAAAGT-TCTGCTAGACAAGGGTATAG-3' | #16 (PI3-HNKpnI) |
| | | #28  3'-ATTAATTAAGGTAGTTTTCA-AGACGATCTG-5' | |
| SN(59-140)d | #27(PI3-HN5'EcoRI) | #41  5'-AGTGCTAATT-TCTGCTAGACAAGGGTATAG-3' | #16 (PI3-HNKpnI) |
| | | #42  3'-AGAAGTAGTATCACGATTAA-AGACGATCTG-5' | |
| SN(80-140)d | #27(PI3-HN5'EcoRI) | #45  5'-TGAGTTTATG-AGCAGGGAGGTGAAAGAGTC-3' | #16 (PI3-HNKpnI) |
| | | #46  3'-CTGCATTTGTTACTCAAATAC-TCGTCCCTC-5' | | been cut with the same enzymes. This recombinant plasmid encodes 140 amino acids at the N-terminal end which are derived from SN-HN and 412 amino acids at the C-terminal derived from PI3-HN. The DNA sequence of the entire coding region which was amplified by PCR with Taq DNA polymerase was verified by sequence analysis using SEQuenase Version 2.0 DNA sequencing Kit (United States Biochemicals, Cleveland, Ohio). Similar procedures to that mentioned above were employed to generate the SN(137) chimera using primer set #5 (SEQ ID NO:1) and #14 (SEQ ID NO:5 and primer set #15 (SEQ ID NO:6) and #16 (SEQ ID NO:7) (PI3-HN KpnI). The PCR product DNA was used to replace the Eco RI-KpnI fragment of SN(140).

Figure 4:
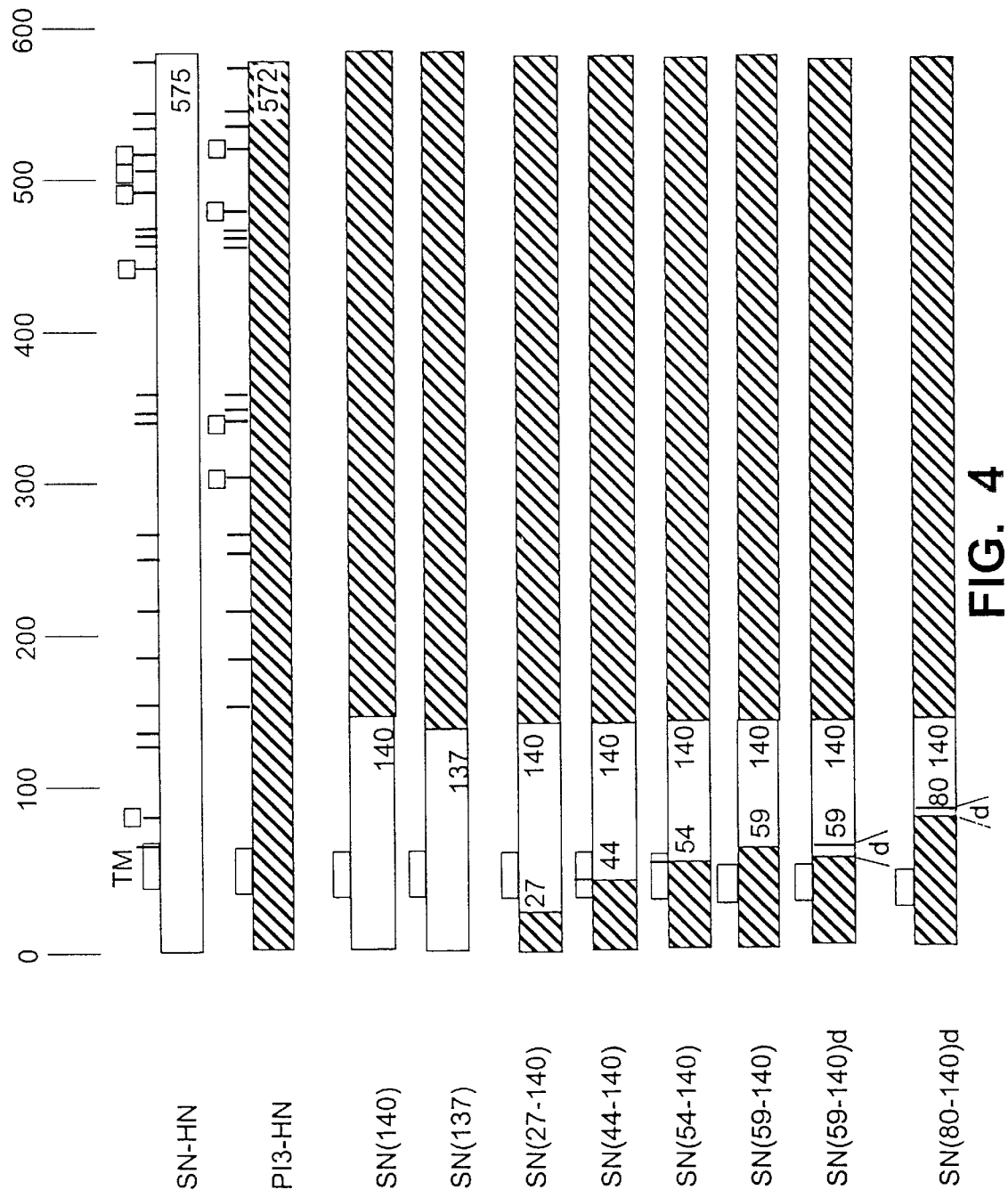
FIG. 4 is a schematic diagram of Sendai virus (SN) and human parainfluenza type 3 virus (PI3) HN proteins, and chimeric HN proteins. The amino acid sequence numbers of the Sendai virus HN are shown above. The transmembrane domain (TM), potential glycosylation sites, and positions of cysteine residues are presented for the wild type HN proteins. Open columns and shaded columns indicate SN HN and PI3-HN sequences, respectively.

A second series of chimeric HN molecules was designed to replace the N-terminal regions such as the cytoplasmic tail or transmembrane domain of SN(140) with PI3-HN sequences. For all of these constructs, primer #27 (SEQ ID NO:8) (PI3HN5'EcoRI) and primer #16 (SEQ ID NO:7) were used as outer primers. The inner chimeric primers used for construction are listed in Table 1. All the final PCR products were digested with EcoR I and Kpn I and inserted into the Eco RI-Kpn I site of the SN(140) recombinant plasmid. The schematic structures of the chimeric HN proteins are shown in FIG. 4 together with those of wild type SN-HN and PI3-HN. Remaining primers shown in Table 1 have sequence ID Nos. as follows:

| Primer # | SEQ ID NO: |
|---|---|
| 25 | 8 |
| 26 | 9 |
| 31 | 10 |
| 32 | 11 |
| 39 | 12 |
| 40 | 13 |
| 29 | 14 |
| 28 | 15 |
| 41 | 16 |
| 42 | 17 |
| 45 | 18 |
| 46 | 19 |

Expression of the chimeric HN proteins. To characterize the chimeric HN proteins, the chimeric HN cDNAs were expressed in HeLa-T4 cells by using the vaccinia T7 RNA polymerase transient expression system. Fifteen hours post-transfection the cells were metabolically labeled with [$^{35}$S]-Met/Cys for 2 h and lysed. The cell extracts were precipitated with anti-SN or anti-PI3 serum followed by SDS-PAGE and fluorography. All of the chimeric HN proteins were found to be precipitated with anti-PI3 antibody, indicating that the chimeric proteins maintain antigenic sites of the PI3-HN proteins. The electrophoretic mobilities of the chimeric proteins were similar to that of the wild type SN-HN except for SN(80-140)d (lane 12)) which lacked a potential glycosylation site (position 77 to 79) in the SN-HN sequence (FIG. 1). This observation suggests that the potential glycosylation site at this position of the SN-HN is actually utilized. When the chimeric proteins were analyzed by SDS-PAGE under non-reducing condition, the high molecular weight bands indicated as 2xHN were observed in all constructs except for wild type PI3-HN. This observation agrees with previous reports that disulfide-linked oligomerization as observed in SN-HN was maintained by the presence of the short SN-HN sequences present in the chimeric HN proteins. Comparison of the location of cysteine residues between chimeric HNs and wild type PI3-HN indicates that the cysteine at position 129 in the SN-HN (second cysteine in the SN-HN in FIG. 1) is responsible for intermolecular disulfide bonds formation. This position is similar to that of a cysteine residue (position at 123) identified in disulfide bond formation between NDV-HN monomers [McGinnes, L. W. et al. (1994) Virology 200:470–483].

Cell surface expression of the chimeric HN proteins. To examine the surface expression levels of the chimera HNs, a surface biotinylation assay was performed. The cell surface proteins of HeLa-T4 cells infected with vTF7-3 and transfected with recombinant plasmid DNAs were biotinylated and immunoprecipitated with specific antibodies to the SN or PI3 viral proteins. After separation by SDS-PAGE, the proteins were blotted onto membranes and visualized by ECL. The membranes were exposed to X-ray films, and each band of interest was quantified by densitometry analysis using the NIH image program. The results were expressed as a percentage of the value obtained for wild-type PI3-HN (Table 2). The SN(140) chimera was detected on the cell surface at a level of 68.1% of that of the PI3 wild type HN proteins. The chimera SN(137), which differs in sequence from the SN(140) chimera by only 3 amino acids, was detected at a somewhat lower level on the cell surface. The second series of chimeric HNs with alterations in their cytoplasmic and/or transmembrane domains was also examined for their cell surface expression and it was found that they were expressed and transported efficiently to

TABLE 2

Cell surface expression and fusion promoting activity of chimeric HN proteins

| HN Chimera | Cell surface expression (%)[a] | Fusion activity (5)[b] | Relative fusion promoting activity b/a |
|---|---|---|---|
| SN-HNwt | 163.9 | 100.00 | 0.61 |
| PI3HNwt | 100.0 | 3.47 | 0.03 |
| SN (140) | 68.1 | 44.64 | 0.66 |
| SN (137 | 48.3 | 0 | 0 |
| SN (27-140) | 75.6 | 79.72 | 1.05 |
| SN (44-140) | 126.6 | 88.67 | 0.70 |
| SN (54-140) | 131.5 | 55.26 | 0.42 |
| SN (59-140) | 82.3 | 8.82 | 0.11 |
| SN (59-140)d | 61.6 | 31.33 | 0.51 |
| SN (80-140)d | 72.0 | 6.72 | 0.09 |

[a]The data were determined from FIG. 3.
[b]All HN proteins were co-expressed with SN-F. The data were determined from FIG. 5.

the cell surface, and maintained the antigenicity of PI3-HN (62 to 132% of wild-type PI3-HN). Examination by indirect immunofluorescent staining also showed that the all chimeric HN proteins were detected on the cell surface (data not shown).

Hemadsorption activity of chimera HN. The HN proteins of paramyxoviruses have hemadsorption (HAD) activity as one of their biological activities, reflecting their ability to bind sialic acid-containing receptors on red blood cells. The cells expressing chimeras (SN(140), SN(44-140), SN(54-140), SN(59-140), and SN(59-140)d showed high levels of hemadsorption like wild type SN-HN or SN(27-140). The chimeras SN(137) and SN(80-140)d showed lower activities. Vector DNA-transfected cells did not adsorb any guinea pig erythrocytes. To quantify the HAD activity, the bound erythrocytes were lysed with 50 mM ammonium chloride and the absorbance measured at 549 nm. The results are shown in FIG. 6 as percentage of wild type SN-HN hemadsorption. The chimeras SN(140), SN(27-140), SN(44-140), SN(54-140), SN(59-140), and SN(50-140)d had comparable or higher HAD activity than that of SN-HN. However, the chimeras SN(137) and SN(80-140)d showed reduced levels of 27.5% and 30.5%, respectively, of the hemadsorption activity of wild type SN-HN. These results demonstrate that all of the chimeric HN proteins were expressed on the cell surface and have detectable receptor binding activities, and the activity was unaffected in most of the chimeric proteins.

Fusion promoting activities of the chimeric HN proteins. Extensive cell fusion was observed in the monolayer cell culture which were transfected with a combination of SN-F and SN-HN and incubated with 0.1 µg/ml trypsin (type XIII, Sigma Chemicals). However, no cell fusion was observed with the heterologous combinations of proteins SN-F and PI3-HN (data not shown). These results are in agreement with those reported previously for other paramyxoviruses, in which paramyxovirus-induced cell fusion was found to require coexpression of HN and F proteins derived from the same virus type [Heminway, B. R. et al. (1995) *Virus Res.* 31:1–16; Horvath, C. M., et al. (1989) *J. Virol.* 66:4564–4569; Hu, X. et al. (1992) *J. Virol.* 66:1528–1534]. To quantitatively analyze the fusion promoting activity of the chimeric HN proteins, a fusion depending reporter gene activation assay was employed [Nussbaum, O. et al. (1994) *J. Virol.* 68:5411–5422; Yao, Q. et al. (1995) *J. Virol.* 69:7045–7053]. HeLa-T4 cells expressing SN-F and chimeric or wild-type HN were cocultivated with HeLa-T4 cells which were transfected with the pG1NT7β-gal plasmid. The mixed cells were incubated at 37° C. for 5 h in the presence of trypsin (0.1 ǁg/ml) to allow cleavage of SN F. Before extraction of β-galactosidase, the cells were observed by microscopy. Syncytium formation was observed in the cells expressing SN(27-140) HN and SN-F. SN(140) HN and SN-F expressing cells showed a lower level of syncytium formation and the cells transfected with vector DNA and SN-F showed no syncytium formation.

Figure 7:
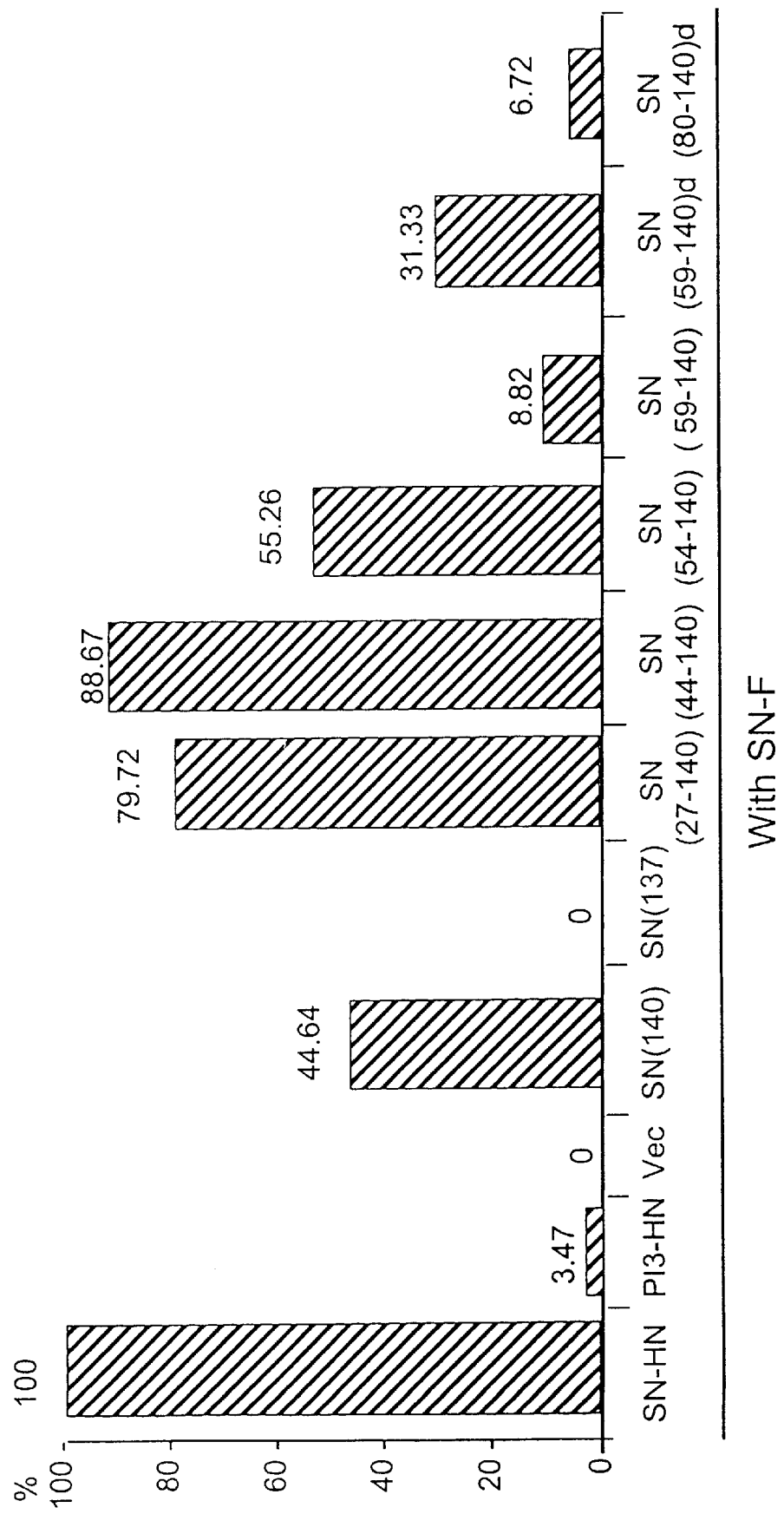
FIG. 7 Fusion induction by co-transfection of SN-F with chimeric HN proteins. Five hours after mixing the F and HN expressing cells and β-gal gene transfected cells, the cells were observed by microscopy. The cells were cotransfected with SN-F and a) SN-HN, b) SN(140), c) SN(27-140), or d) vector DNA. Quantitative colorimetric assay of the fusion induction by SN-F and chimeric HN proteins data are presented as the percentage of β-galactosidase production of the cells cotransfected with SN-F and SN-HN.

The results of the colorimetric assay of β-galactosidase production are shown in FIG. 7. The data are presented as a percentage of the β-galactosidase production in the cells transfected with wild type SN-HN and SN-F. The first chimera we tested, SN(140), showed 44.6% of the wild type level of fusion promoting activity, but the SN(137) chimera did not show any significant fusion promoting activity. This result indicates that the three amino acid residues located between position 140 and 137 are critical for the type specific fusion promotion activity with the SN-F protein. The SN(27-140), SN(44-140), and SN(54-140) HN chimeras have segments replaced by PI3-HN sequences in the cytoplasmic tail or cytoplasmic half of the transmembrane domain, respectively. All of these three chimeric HNs were found to promote the cell fusion with SN-F with activities of 79.7%, 88.7% and 55.3% of the wild type SN-HN, respectively. However, a chimera SN(59-140) in which the whole cytoplasmic tail and transmembrane domain of SN-HN were replaced by PI3-HN showed very low activity (8.8% of wild-type HN). This construct, SN(59-140), contains a 5 amino acid PI3 sequence in the ectodomain adjacent to the transmembrane domain (amino acid positions 54 to 58 of PI3-HN). To examine the possibility that this fragment may affect the structure of the chimeric HN required for promoting cell fusion of SN-F, another chimera SN(59-140)d was constructed and examined for fusion promoting activity. The activity was found to be restored to 31.3% of wild type level. This observation indicates that the length of the external domain of HN as well as the precise amino acid sequence is important for the type specific interaction with the F protein. The construct SN(80-140)d lost almost all fusion promotion activity (6.7%) although the protein was expressed on the cell surface and showed HAD activity (FIG. 3 and FIG. 4). The fusion activities were normalized for cell surface expression levels, and the relative fusion promoting activities of the chimeric HN molecules are presented in Table 2. SN(140), SN(44-140), SN(54-140), and SN(59-140)d showed comparable activity, scores of 0.42 to 0.7, to SN-HN (0.61). The SN(27-140) and SN(80-140)d constructs showed levels of only 0.11 and 0.09, respectively. All of these results indicate that the region from aa 59 to 140 (82 amino acids) of the HN molecule is the most important one for the promotion of cell fusion by the Sendai virus F protein.

We have constructed and expressed chimeric HN proteins between the SN-HN and PI3-HN proteins with the objective of defining the minimal segment of the SN-HN protein that will promote cell fusion in a virus-type specific manner. We observed that one chimera SN(140) could promote cell fusion of SN-F but a very similar chimera SN(137) could not even though both proteins were expressed on the cell surface and showed receptor binding activity. This result indicates that the region located between residues 140 and 137 in the SN-HN plays a critical role for the type specific fusion promotion activity with the Sn-F protein. Another chimeric HN, (SN(59-140)d in which the entire cytoplasmic and transmembrane domain were replaced by PI3-HN sequences also maintained fusion promotion activity. However, SN(80-140)d in which additional PI3-HN sequences were substituted failed to induce cell fusion with SN-F. These results indicate that the cytoplasmic domain and transmembrane domain as well as most of the external domain can be replaced by a heterologous type viral HN sequence, and that a segment including 82 amino acids (position 59 to 140 of SN-HN) is the most important region for virus-type specific fusion promoting activity of Sendai virus. This region includes a region previously identified in a deletion mutant of NDV-HN which lacked fusion promotion activity (amino acid positions 91 to 99) [Sergel, T. (1993) *Virology* 196:831–834; Sergel, T. (1993) *Virology* 193:717–726] as well as the mutation site in antibody escape mutants of PI2-HN (positions 83 or 91) [Yuasa, T., et al. (1995) *Virology* 206:1117–1125].

Recently, analysis of chimeric HN proteins was reported for the combination of PI1 and SN(2), and it was concluded that the middle 62%, which included much of the predicted globular domain, is responsible for the fusion-promotion activity. In addition, the fusion promotion activity of HN mutants in a cysteine residue at position 55 located in the transmembrane region were examined [Bousse, T., et al. (1994) *Virology* 204:506–514]. A Cys to Try mutant abolished fusion promotion activity, but a Cys to Gly mutant maintained the activity. We found that a chimeric HN protein, SN(59-140)d, which lacks the cysteine residue at the corresponding position, efficiently promoted cell fusion. This result demonstrates that this specific residue is not required for fusion promotion activity, and that the entire transmembrane domain sequence can be functionally replaced by that of a heterologous type HN.

In a recent study of chimeric HN proteins between NDV and PI3 [Deng, R. et al (1995) *Virology* 209:457–469], the transmembrane domain and 82 or 93 amino acids of the N-terminal; ectodomain of HN were required to induce fusion with F derived from same type virus. This portion of the ectodomain is similar to that found here for SN-HN (the first 82 amino acids in the extracellular domain), but the reported requirement for the transmembrane domain differs from our results. In another recent study, it was concluded that a region located at the membrane-proximal end of the ectodomain of PI2-HN (58 amino acids) and the N-terminal 94 amino acids of the SV41-HN protein were important for type-specific fusion promotion [Tsurudome, M., et al. (1995) *Virology* 213:190–203]. The observed differences in requirement for the transmembrane domain and different lengths of the ectodomain may depend on the precise sequences present in the HN proteins. There may also be differences among HN proteins in the precise sequence required for fusion promotion activity.

EXAMPLE 8

Peptides Derived from F Protein. Peptide Synthesis. Peptides were synthesized on a Rainin Symphony Multiplex multiple peptide synthesizer (Rainin Instruments Company, Mass.). Using standard solid-phase synthesis techniques, all peptides were acetylated at the N terminus and amidated at the C terminus. Cleavage of peptides from the resin and removal of side-chain blocking groups were automatically performed on the instrument with trifluoroacetic acid and scavengers (5% thioanisol, 5% water, 2.5% ethanedithiol, 0.8 M phenol). The peptides were then washed with 12 ml cold either for 4 times, dissolved in water, and dried under vacuum overnight. Peptides were dissolved in deionized water.

Inhibition of plaque formation. A series of 2-fold dilutions of F peptides together with appropriately diluted PI2 or PI3 virus were added to monolayers of Vero cells. After 1 h incubation at 37° C., the inoculum was removed and overlaid with 2% white agar mixed at 1:1 ratio with 2XDMEM containing 2% FBS. Three days after overlying, red agar mixed at a 1:1 ratio with 2XDMEM containing 2% FBS was overlaid to stain the cells. Plaque numbers were counted one day after neutral red staining and recorded. The Reed-Muench method of estimating 50% endpoint [Welkos, S. et al., (1994) *Methods in Enzymology*. 235:29–39] was used to calculate the F peptide 50% effective concentration ($EC_{50}$) value.

Surface immunofluorescence. Indirect immunofluorescence was performed as described by Paterson et al. 1989. In general, HeLa-T4 cells were grown on glass coverslips in 24-well plates and infected with wild-type PI2 virus as described above. At indicated times post infection, cells were washed with ice-cold PBS three times before being fixed with 1% paraformaldehyde in PBS. Rabbit anti-PI2 antibody was added onto cell monolayers, and cells were then incubated at 4° C. for 30 min. Cells were washed with ice-cold PBS three times, and then goat anti-rabbit immunoglobulin G fluorescein-conjugated antibody (Southern Biotechnology Associates, Inc., Birmingham, Ala.) was added and was then incubated at 4° C. for 30 min. Cell surface fluorescence was examined by fluorescence microscopy with a Nikon Optiphot microscope.

Figure 8A:
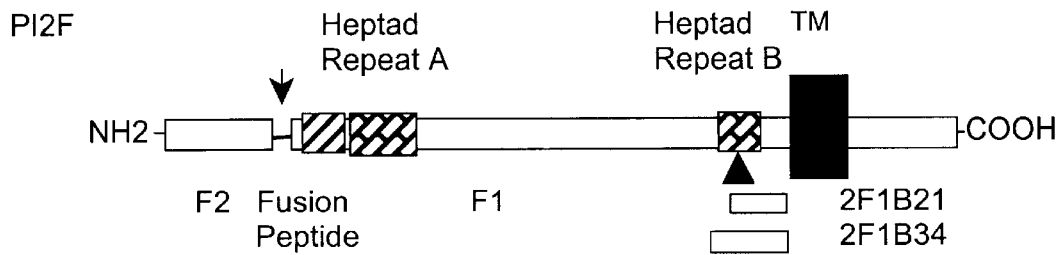
FIGS. 8A–8B Schematic diagram of the F proteins of PI2 and PI3 viruses and amino acid sequences of the synthetic F peptides. (A) Full length PI2F and amino acid sequences of peptides 2F1B21 and 2F1B34 are shown; ▲ represents a predicted glycosylation site within the heptad repeat B region. Arrows represent cleavage sites. TM, transmembrane domain. (B) Full length PI3F and amino acid sequences of peptides 3F1B24 and 3F1B35 are shown.

Peptides derived from the F protein heptad repeat B inhibit virus-induced cell fusion. Several reports have indicated that conserved heptad repeat regions in the paramyxoviruses fusion protein are essential for viral fusion activity [Buckland R. et al. (1992) *J. Gen Virol*. 73:1703–1707; Sergel T. G. et al, (1994) *J. Virol*. 68:7654–7658; Reitter J. N. et al., (1995) *J. Virol*. 69:5995–6004]. In order to study the role of this region in parainfluenza virus-induced cell fusion, a series of synthetic peptides corresponding to the heptad repeat B region near the transmembrane domain of the fusion protein was synthesized. FIG. 8 shows a schematic diagram of two peptides (2F1B21 [SEQ ID NO:20] and 2F1B34 [SEQ ID NO:21]) from the PI2F sequence. 2F1B21 (21 a.a.) (SEQ ID NO:20) extends from the beginning of the transmembrane domain to a predicted glycosylation site in the heptad repeat B region, while 2F1B34(35 a.a.) (SEQ I.D. NO:21) extends from the beginning of the transmembrane domain to include the entire heptad repeat B region. Similarly, for PI3 virus (FIG. 8), peptide 3F1B24(24 a.a.) (SEQ ID NO:22) corresponds to the heptad repeat B only, while 3F1B35 (35 a.a.) (SEQ ID NO:23) extends from the beginning of the transmembrane domain to include the entire heptad repeat B.

To determine whether these peptides have the potential to inhibit virus-induced cell fusion, the extent of cell fusion was compared at 24 h post viral infection in infected cells incubated with or without the peptides. In HeLa-T4 cells infected with PI2 virus at m.o.i. of 0.1, cell fusion was reduced remarkably when incubated with 2F1B21 (SEQ ID NO:20) peptide at 24 h post infection at concentration of 200 $\mu$M or more, while cell fusion was completely inhibited by the 2F1B34 (SEQ ID NO:21) peptide at a concentration as low as 80 $\mu$M. Similarly, in PI3 virus-infected HeLa-T4 cells, the longer peptide 3F1B35 (SEQ ID NO:23) completely inhibited virus-induced cell fusion at concentration of 100 $\mu$M, while the shorter peptide 3F1B24 (SEQ ID NO:22) partially inhibited cell fusion at 200 $\mu$M or more. Extensive syncytia were observed in HeLa-T4 cells infected with either the PI2 or PI3 wt virus. Syncytium formation was dramatically decreased in HeLa-T4 cells infected with the virus and then incubated with the shorter peptides 2F1B21 (SEQ ID NO:20) or 3F1B24 (SEQ ID NO:22)k, whereas no syncytia were seen in infected cells incubated with the longer peptides 2F1B34 (SEQ ID NO:21) or 3F1B35 (SEQ ID NO:23). These results demonstrate that peptides corresponding to the heptad repeat B have the potential to inhibit virus-induced cell fusion, and the sequences between the transmembrane domain and the heptad repeat B are also important for maximum inhibitory activity.

Inhibition of cell fusion is virus type specific. To determine the specificity of the inhibition of virus-induced cell fusion, HeLa-T4 cells were infected with one virus type and incubated with F peptides derived from the F protein of another virus type. The inhibition of cell fusion was observed at 24 h post infection. As shown in Table 3, peptides corresponding to PI2F sequences can only inhibit cell fusion induced by PI2 but not PI3. Similarly, peptides from PI3F can only inhibit cell fusion induced by PI3 but not PI2 virus. In addition, none of the peptides from PI2 or PI3 could inhibit cell fusion induced by simian virus 5(SV5). These results demonstrate that the presence of a leucine zipper-like motif alone is not the only requirement for inhibitor y activity, but that the specific amino acid sequences from the heptad repeat B to the transmembrane domain for each virus type also play an important role in the inhibitory activity of the F peptides.

TABLE 3

Inhibition of virus-induced cell fusion by synthetic peptides is virus type specific[a]

|  | 2F1B21 | | 2F1B34 | | 3F1B24 | | 3F1B35 | |
| --- | --- | --- | --- | --- | --- | --- | --- | --- |
| Viruses | + | − | + | − | + | − | + | − |
| PI2 | + | +++[b] | − | +++ | +++ | +++ | +++ | +++ |
| PI3 | +++ | +++ | +++ | +++ | + | +++ | − | +++ |
| SV5 | +++ | +++ | +++ | +++ | +++ | +++ | +++ | +++ |

[a]Hela-T4 cells were infected with PI2 or PI3 at m.o.i. of 0.1. After virus absorption at 37° C. for 1 h, the inoculum was removed and replenished with 2.5% DMEM with (+) or without (−) addition of peptides. Cell fusion extent was observed 24 h post infection.
[b]+++: >60% of nuclei are present in syncytia. +: <20% of nuclei are present in syncytia. −: no syncytia were seen.

Peptides derived from the F protein inhibit cell fusion by vaccinia-T7 expressed F and HN proteins. In order to confirm that the synthetic F peptides inhibit cell fusion by interaction with viral glycoproteins and that they are not acting on other steps in the viral replication cycle, the vaccinia-T7 transient expression system was used to express homologous F and HN with or without addition of the peptide inhibitor in the culture media. In Table 4, HeLa-T4 cells were infected with recombinant vaccinia virus-T7 (vTF7.3) and then transfected with homologous F and HN genes. Six hours post transfection, F peptides were added to the culture media. Inhibition of F and HN induced cell fusion was observed at 18 hr in the wells incubated with the F peptides. Similar to results obtained with virus infection, 2F1B34 (SEQ ID NO:21) (at concentration of 400 $\mu$M) can completely inhibit cell fusion induced by coexpression of PI2 F plus PI2 HN and 3F1B35 (SEQ ID NO:23) (at concentration of 800 $\mu$M) can inhibit

TABLE 4

Inhibition of cell fusion induced by vaccinia-expressed F. and HN proteins[a]

|  | 2F1B21 | | 2F1B34 | | 3F1B24 | | 3F1B35 | |
| --- | --- | --- | --- | --- | --- | --- | --- | --- |
| Plasmids | + | − | + | − | + | − | + | − |
| PI2F + PI2HN | + | +++[b] | − | +++ | +++ | +++ | +++ | +++ |
| PI3F + PI3HN | +++ | +++ | +++ | +++ | + | +++ | − | +++ |
| SV5F + SV5HN | +++ | +++ | +++ | +++ | +++ | +++ | +++ | +++ |

[a]Hela-T4 cells were infected with vTF7.3 at m.o.i. of 5 at 37° C. for 1 hr, then cells were transfected with homologous F and HN genes. Six hours post transfection, F peptides were added to the culture media. Inhibition of cell fusion was observed 18 h post transection.
[b]+++: >60% of nuclei are present in syncytia. +: <20% of nuclei are present in syncytia. −: no syncytia were seen.

fusion by PI3 F plus PI3 HN, respectively, while 2F1B21 (SEQ ID NO:20) and 3F1B24 (SEQ ID NO:22) only partially inhibited cell fusion. From these results, we conclude that peptides corresponding to heptad repeat B have the potential to inhibit virus-induced cell fusion by interacting with the viral glycoproteins.

Figure 9:
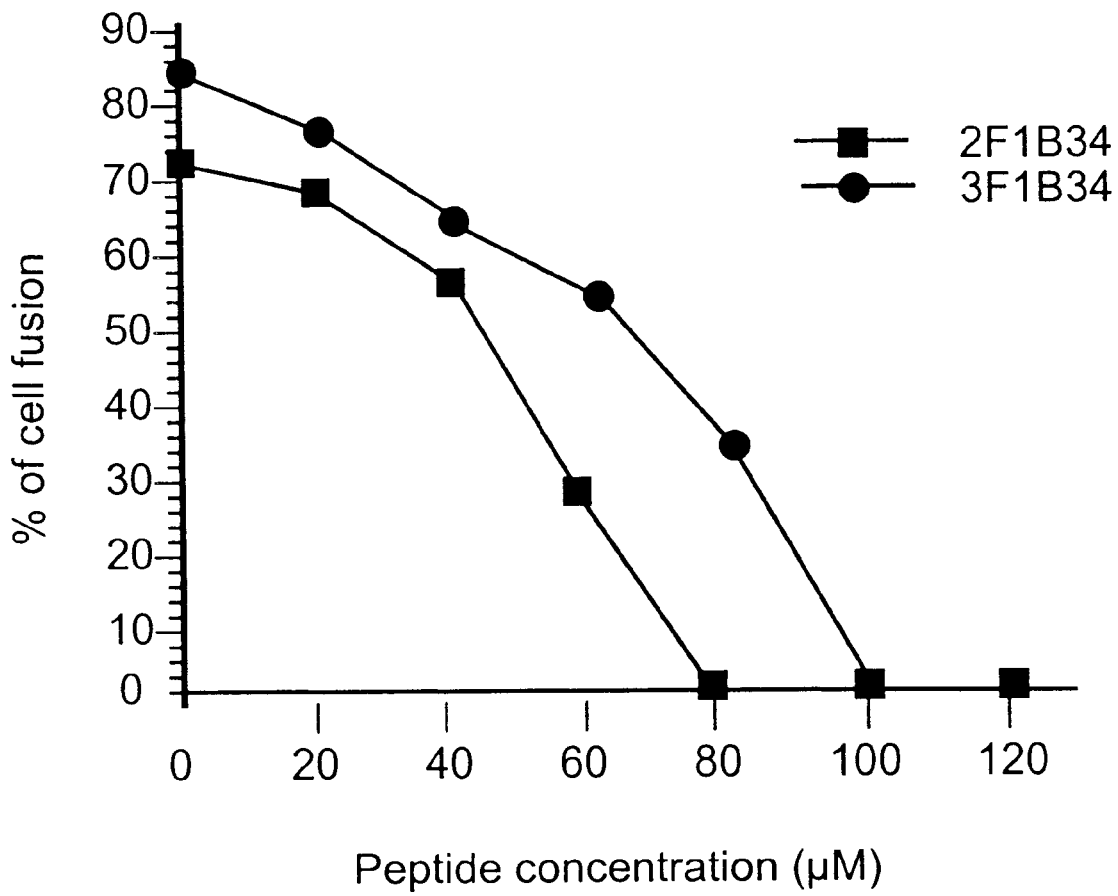
FIG. 9 Dose-dependent inhibition of cell fusion by F peptides. HeLa-T4 cells were infected with PI2 or PI3 virus at 37° for 1 h, and peptides were added post absorption. Inhibition of cell fusion was observed at 24 h post infection. Cell fusion was measured by polykaryon formation and expressed as (number of nuclei in polykaryons/number of total nuclei)×100. Cells were counted in five different fields under a light microscope.

Inhibition of cell fusion is dose dependent. To determine the dose dependence of inhibition of cell fusion, increasing concentrations of peptides were added to the culture medium and the effect on cell fusion was determined. FIG. 9 shows the dose response curves for the longer peptides 2F1B34 (SEQ ID NO:21) from PI2F and 3F1B35 (SEQ ID NO:23) from PI3F. The shorter peptides 2F1B21 (SEQ ID NO:20) from PI2 and 3F1B24 (SEQ ID NO:22) from PI3 could only partially inhibit cell fusion even at peptide concentrations as high as 1.2 mM (data not shown). This indicates again that no only the heptad repeat B but also sequences between heptad repeat B and the transmembrane domain are required to completely inhibit virus-induced cell fusion.

F peptides inhibit viral spread. To determine whether the F peptide interferes with the viral entry process, a plaque assay was performed by inoculating cells with virus and peptide together at 37° C. for 1 h, and then overlaying with agar without the addition of peptide. At $10^4$ dilution of the PI2 virus stock, 80 $\mu$M of the 2F1B34 peptide (SEQ ID NO:21) caused an 80% reduction in number of plaques. Similarly, at $10^5$ dilution of the PI3 virus stock, 100 $\mu$M of the 3F1B35 peptide (SEQ ID NO:23) caused a 70% reduction in number of plaques. Furthermore, the reduction in the number of viral plaques was correlated with increasing concentration of peptide incubated with the virus. Using this method, the 50% effective concentration ($EC_{50}$) of F peptides that inhibit the virus infection efficiency was determined by the Reed-Muench method as described in Materials and Methods. The $EC_{50}$ value for 2F1B34 (SEQ ID NO:21) is 53.8 $\mu$M and for 3F1B35 (SEQ ID NO:23) is 81.6 $\mu$M. These data indicate that the F peptides may inhibit the viral entry process.

Figure 10:
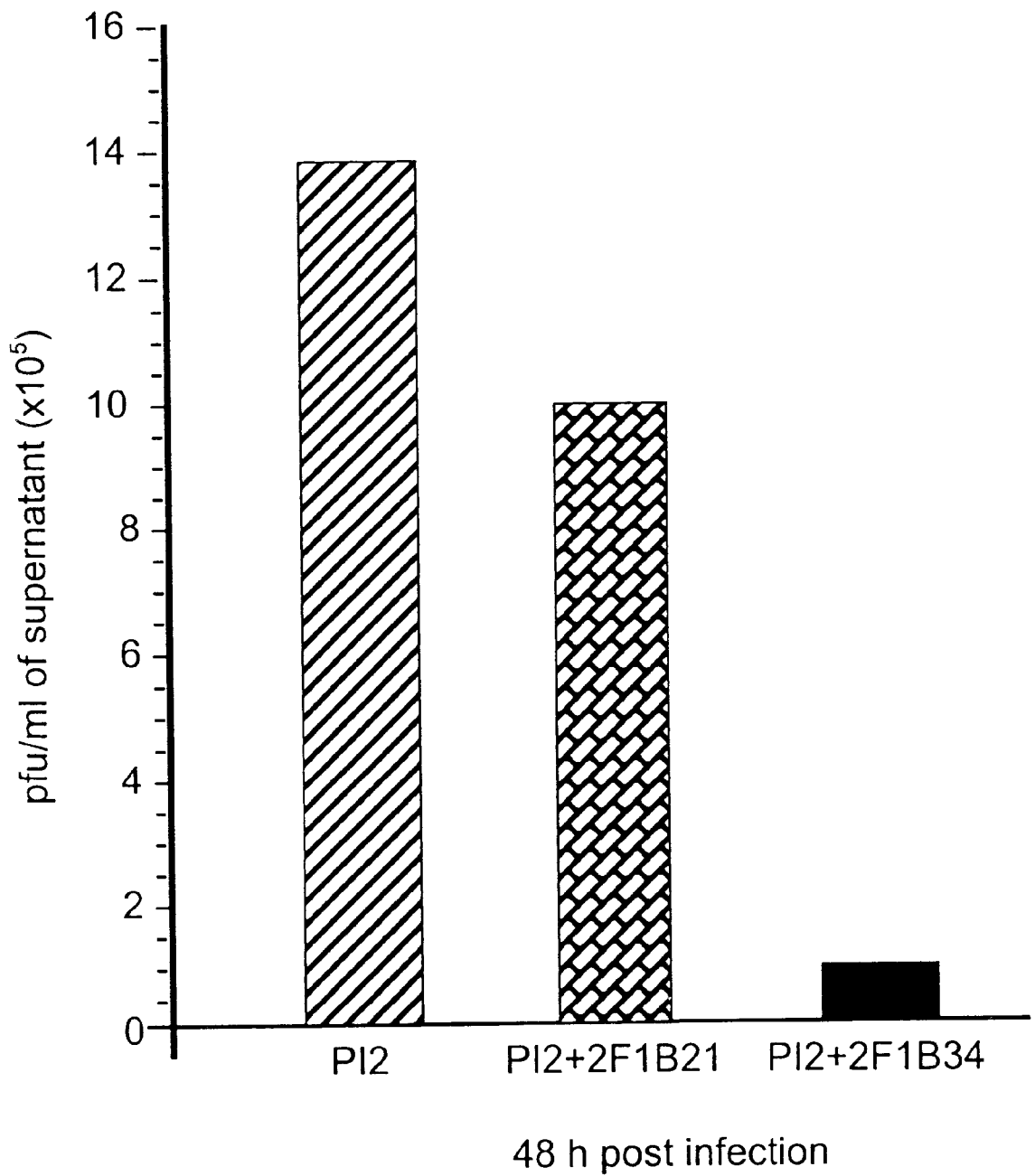
FIG. 10 Inhibition of virus production by F peptides. HeLa-T4 cells were infected with PI2 virus a m.o.i. of 0.1. After incubation at 37° C. for 1 h, the inoculum was removed and 2.5% DMEM was added with or without addition of 80 μM of the synthetic peptides 2F1B21 and 2F1B34. Released virus titers were determined by plaque assay 48 h post infection.

We also compared viral titers in the culture supernatant incubated with or without peptides at 18 h, 24 h, and 48 h post virus infection at low m.o.i. of 0.1. Although the virus titer was not remarkably reduced in the supernatant incubated with the peptide at 18 and 24 h post infection, a 15-fold decrease in the viral titer was observed at 48 h post PI2 infection in the presence of 2F1B34 (SEQ ID NO:21) (FIG. 10)k. Similarly, the 3F1B34 peptide (SEQ ID NO:23) caused a 10 fold reduction in PI3 virus titers (not shown)(. The effect of 2F1B21 (SEQ ID NO:20) and 3F1B24 (SEQ ID NO:22) on multiple cycle growth was not as dramatic as 2F1B34 (SEQ ID NO:21) and 3F1B35 (SEQ ID NO:23).

Figure 11A:
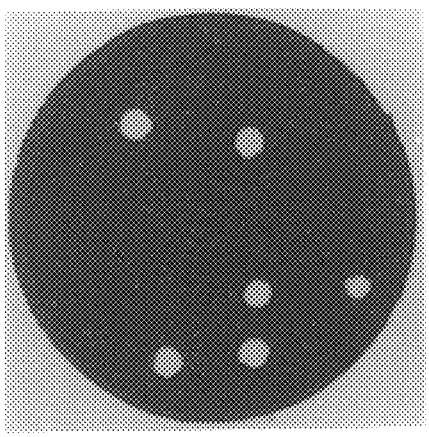
FIGS. 11A and 11B Plaque size reduction by F peptides. Plaque assay was performed on the Vero cells using PI2 virus. After 1 h absorption at 37° C., inoculum was removed and cells overlaid with a 1:1 mixture of 2% white agar with 2XDMEM containing 2% FBS (A) without addition of F peptide, or (B) with addition of 80 μM of 2F1B34 in the overlay agar. Three days after overlaying, the agar was removed and the monolayer of cells was stained with crystal violet.
Figure 11B:
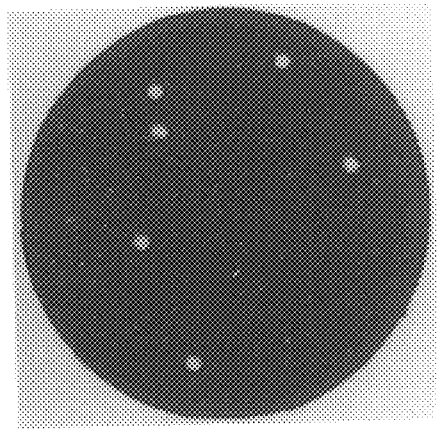

As another indication of a reduction in spread of virus under condition of multiple cycle replication, the effect of the peptides on plaque size was determined. As shown in FIG. 11, when the longer PI2-F peptide was added to the agar overlay after the initial 1 h virus absorption period, the plaque size was reduced from 3 mm in diameter in control cells to 1.5 mm in the presence of the 2F1B34 (SEQ ID NO:21) peptide. This result indicates that the synthetic peptide can inhibit multiple cycle replication of the virus, thus restricting viral spread.

To further confirm that the F peptides inhibit viral spread, we examined the distribution of infected cells by surface immunofluorescence at intervals post low m.o.i. infection in the presence or absence of F peptides. At 18 hpi, cells infected with PI2 virus showed limited cell surface fluorescence of PI2 antigen, but the levels of PI2 antigen expressed on the cell surface increased by 24 and 48 hpi. In contrast, only few cells were expressing PI2 antigen at 18 h when incubated with peptide 2F1B34 (SEQ ID NO:21), and there was no increase in numbers of cells showing antigen expression on the surface at 24 h and 48 hpi. These data indicate that in the presence of the F peptides, the infection process remains limited to the cells initially infected by the inoculum virus.

We have observed that synthetic peptides which include a heptad repeat B sequence in the F1 subunit are specific inhibitors of PI2- or PI3-induced membrane fusion. The high specificity of their inhibitory effect was shown by the finding that each peptide was only able to inhibit fusion by the virus with the same F. protein sequence, i.e., peptides derived from PI2F will inhibit fusion by PI2 virus but not PI3 virus, and vice versa. The most active peptides extended from the second heptad repeat to the beginning of the transmembrane domain (34 a.a. for PI2F and 35 a.a. for PI3F). The peptides were found to inhibit fusion by virus-infected cells as well as vaccinia-expressed F and HN proteins, and also inhibit multiple cycle replication of the virus.

In Sendai virus [Rapaport, D. et al. (1995) *EMBO J.* 14:5524–5531], peptides located near the fusion peptide (similar to DP-197) did not have an anti-viral effect while peptides derived from the leucine zipper region in the F protein adjacent to the transmembrane anchor (similar to DP-178) were reported to be inhibitors of the fusion of Sendai virus with human erythrocytes. These results suggest that the highly conserved structural features of this region potentially play a similar role in a broad range of fusogenic viruses.

We observed that peptides which extend from the heptad repeat B to the beginning of the transmembrane domain were more potent inhibitors of virus induced cell fusion. Moreover, the F peptides derived from one virus could only inhibit cell fusion induced by this specific virus but not others. The specificity of peptides derived from P12F compared with PI3 and SV5 are presumably related to differences in the envelope sequences of the corresponding regions of these viruses. Sequence comparison of these regions showed no sequence homology except for a common leucine zipper-like motif which has the potential to form a coiled coil secondary structure. Studies of the F interaction sites in the HN protein demonstrated that an 82 amino acid region just outside the membrane-spanning region of the HN protein of SN virus is sufficient for almost full fusion activity when coexpressed with the SN F protein (Example 7). Other recent studies with other paramyxoviruses (NDV and PI2) have identified a similar region of HN involved in fusion promotion [Deng, R. et al. (1995) *Virology* 209:457–469; Tsurodome, M. et al, (1995) *Virology* 213:190–203]. Although there are not yet any reports on the F-HN interaction regions in F proteins, it is likely that HN could interact with the corresponding sequences in the F protein which are just external to the transmembrane region. The heptad repeat B region and the sequences between the heptad repeat B and transmembrane domain are therefore involved in F-HN interaction.

We observed that the F peptides showed an inhibitory effect on viral entry as well as the spread of infection after low m.o.i. inoculations. The peptides therefore appear to block fusion of the virus to the cell. Furthermore, the peptides similarly interfere with spread of infection either by blocking cell-cell fusion, or subsequent rounds of virus to cell fusion. The HIV-1 peptide DP-178 which corresponded to the leucine zipper motif near the N-terminus of transmembrane domain was a more potent inhibitor of cell-cell fusion than of infection by cell-free virus [Wild, C. T. et al (1994a) *Proc. Nati. Acad. Sci.* 91:9770–9774]. Although the reason for the difference in potency of DP-178 in these two process is unclear, it may reflect differences in the processes of cellfree virus transmission vs. cell to cell transmission. Studies on mumps virus-induced cell fusion also indicated that the mechanisms of cell-cell fusion seems different from virus-cell fusion [Tanabayashi, K. et al. (1993) *J. Virol* 67:2928–2931].

Many peptides have short half lives when administered systemically. Because the F-peptides are interacting with the external domains of the viral envelope proteins, it is likely that they act at the surfaces of infected cells, and thus prevent virus spread during multiple cycles of infection. Therefore, the F-peptides would inhibit virus infection when administered to the respiratory tract by aerosol. This provides a method for inhibiting virus infection in vivo, which can lead to control of the serious respiratory diseases in infants which result from parainfluenza virus infections.

The invention as described herein is applicable throughout the range of paramyxoviruses, as will be understood from the knowledge that HN and F proteins or their counterparts are common features of all paramyxoviruses and have common functions in the infection process. Although the invention has been disclosed with reference to HN:F expressed in certain cell lines and isolated by certain means, the invention includes HN:F without regard to source cells and without regard to method of purification, although it will be understood that more highly purified forms of HN:F are generally less likely to contain undesired contaminants and interfering substances and are therefore generally preferred.

We claim:

1. A peptide having the amino acid sequence of SEQ ID NO:20.

2. A peptide having the amino acid sequence of SEQ ID NO:21.

3. A peptide having the amino acid sequence of SEQ ID NO:22.

4. A peptide having the amino acid sequence of SEQ ID NO:23.

* * * * *

UNITED STATES PATENT AND TRADEMARK OFFICE
CERTIFICATE OF CORRECTION

PATENT NO. : 5,969,094
DATED : October 19, 1999
INVENTOR(S) : Compans and Yao

It is certified that error appears in the above-identified patent and that said Letters Patent is hereby corrected as shown below:

Title page,
Item [56], OTHER PUBLICATIONS, under reference "Blumberg et al," for the year of the publication *Cell*, delete "1995" and replace with -- 1985 --.

Figure 8B:
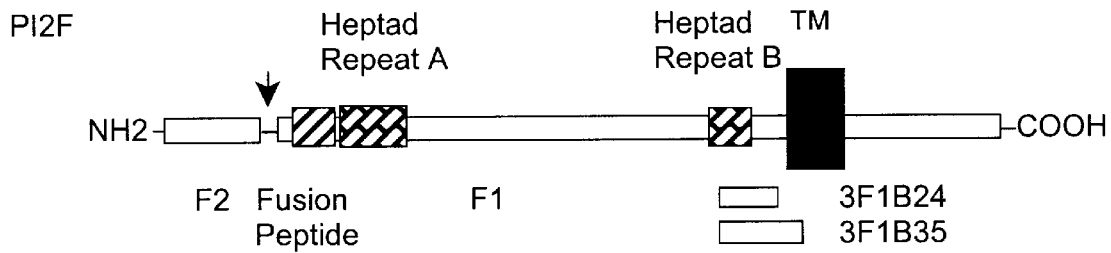

Drawings,
Fig. 8B, at the beginning of the last line, delete "3F1B34" and replace with -- 3F1B35 --.
Fig. 9, following —●— in the legend, delete "3F1B34" and replace with -- 3F1B35 --.

Column 23,
Line 31, delete "(0.1 ǁg/ml)" and replace with -- (0.1$\mu$g/ml) --.

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (xi) SEQUENCE DESCRIPTION: SEQ ID NO:1:

TACGAATTCA TCATGGATGG TGATAGGGGC A                                        31

(2) INFORMATION FOR SEQ ID NO:2:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (xi) SEQUENCE DESCRIPTION: SEQ ID NO:2:

ATCATGTGTT ATTCTACTCT CACAGAGCTG AGTGAG      36

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:3:

CAGCTCTGTG AGAGTAGAAT AACACATGAT GTGGGC      36

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:4:

GACGGATCCT TAACTGCAGC TTTTTGGAAT      30

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:5:

ATTCTTTGTG GAGGGAGCTG AGTGAGCTCT TGTCTG      36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:6:

```
GAGCTCACTC AGCTCCCTCC ACAAAGAATA ACACAT                                    36

(2) INFORMATION FOR SEQ ID NO:7:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (xi) SEQUENCE DESCRIPTION: SEQ ID NO:7:

TAAGTCAGGT ACCAAGTCTG                                                      20

(2) INFORMATION FOR SEQ ID NO:8:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (xi) SEQUENCE DESCRIPTION: SEQ ID NO:8:

TCATGGCAAC TGGGAGAGGT CAAGTAAAGT                                           30

(2) INFORMATION FOR SEQ ID NO:9:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (xi) SEQUENCE DESCRIPTION: SEQ ID NO:9:

ACCTCTCCCA GTTGCCATGA GTAGCCATGG                                           30

(2) INFORMATION FOR SEQ ID NO:10:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (xi) SEQUENCE DESCRIPTION: SEQ ID NO:10:

CCTGGTGTTA CAGTGGGCTT TGTCAATTGC                                           30

(2) INFORMATION FOR SEQ ID NO:11:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: other nucleic acid
```

(iii) HYPOTHETICAL: NO (xi) SEQUENCE DESCRIPTION: SEQ ID NO:11:

AGCCCACTGT AACACCAGGA TTATTGTCC                                                29

(2) INFORMATION FOR SEQ ID NO:12:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:12:

AGTGCTAATT ATCTGTATCA TAATTTCTGC                                               30

(2) INFORMATION FOR SEQ ID NO:13:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:13:

TGATACAGAT AATTAGCACT ATGATGAAGA                                               30

(2) INFORMATION FOR SEQ ID NO:14:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:14:

CATCAAAAGT TCTGCTAGAC AAGGGTATAG                                               30

(2) INFORMATION FOR SEQ ID NO:15:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (xi) SEQUENCE DESCRIPTION: SEQ ID NO:15:

GTCTAGCAGA ACTTTTGATG GAATTAATTA                                               30

(2) INFORMATION FOR SEQ ID NO:16:

(i) SEQUENCE CHARACTERISTICS:
         (A) LENGTH: 30 base pairs (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:16:

AGTGCTAATT TCTGCTAGAC AAGGGTATAG                                          30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:17:

GTCTAGCAGA AATTAGCACT ATGATGAAGA                                          30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:18:

TGAGTTTATG AGCAGGGAGG TGAAAGAGTC                                          30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:19:

CTCCCTGCTC ATAAACTCAT TGTTTACGTC                                          30

(2) INFORMATION FOR SEQ ID NO:20:

(i) SEQUENCE CHARACTERISTICS:
        (A) LENGTH: 21 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:20:

Lys Ser Ala Glu Asp Trp Ile Ala Asp Ser Asn Phe Phe Ala Asn Gln
1               5                   10                  15

```
Ala Arg Thr Ala Lys
            20

(2) INFORMATION FOR SEQ ID NO:21:

(i) SEQUENCE CHARACTERISTICS:
          (A) LENGTH: 34 amino acids
          (B) TYPE: amino acid
          (C) STRANDEDNESS: single
          (D) TOPOLOGY: Not Relevant (ii) MOLECULE TYPE: peptide (iii) HYPOTHETICAL: NO (xi) SEQUENCE DESCRIPTION: SEQ ID NO:21:

Asp Leu Ser Asn Gln Ile Asn Ser Ile Asn Lys Ser Leu Lys Ser Ala
1               5                  10                  15

Glu Asp Trp Ile Ala Asp Ser Asn Phe Phe Ala Asn Gln Ala Arg Thr
            20                  25                  30

Ala Lys (2) INFORMATION FOR SEQ ID NO:22:

(i) SEQUENCE CHARACTERISTICS:
          (A) LENGTH: 24 amino acids
          (B) TYPE: amino acid
          (C) STRANDEDNESS: single
          (D) TOPOLOGY: Not Relevant (ii) MOLECULE TYPE: peptide (iii) HYPOTHETICAL: NO (xi) SEQUENCE DESCRIPTION: SEQ ID NO:22:

Glu Leu Asn Lys Ala Lys Ser Asp Leu Glu Glu Ser Lys Glu Trp Ile
1               5                  10                  15

Arg Arg Ser Asn Gln Lys Leu Asp
            20

(2) INFORMATION FOR SEQ ID NO:23:

(i) SEQUENCE CHARACTERISTICS:
          (A) LENGTH: 35 amino acids
          (B) TYPE: amino acid
          (C) STRANDEDNESS: single
          (D) TOPOLOGY: Not Relevant (ii) MOLECULE TYPE: peptide (iii) HYPOTHETICAL: NO (xi) SEQUENCE DESCRIPTION: SEQ ID NO:23:

Glu Leu Asn Lys Ala Lys Ser Asp Leu Glu Glu Ser Lys Glu Trp Ile
1               5                  10                  15

Arg Arg Ser Asn Gln Lys Leu Asp Ser Ile Gly Asn Trp His Gln Ser
            20                  25                  30

Ser Thr Thr
        35
```